(12) United States Patent
Kousoulas

(10) Patent No.: US 8,586,028 B2
(45) Date of Patent: Nov. 19, 2013

(54) SYNTHETIC HERPES SIMPLEX VIRUSES TYPE-1 FOR TREATMENT OF CANCERS

(75) Inventor: Konstantin G. Kousoulas, Baton Rouge, LA (US)

(73) Assignee: Board of Supervisors of Lousiana State University and Agricultural and Mechanical College, Baton Rouge, LA (US)

( * ) Notice: Subject to any disclaimer, the term of this patent is extended or adjusted under 35 U.S.C. 154(b) by 725 days.

(21) Appl. No.: 12/598,937

(22) PCT Filed: May 9, 2008

(86) PCT No.: PCT/US2008/063206
§ 371 (c)(1),
(2), (4) Date: May 24, 2010

(87) PCT Pub. No.: WO2008/141151
PCT Pub. Date: Nov. 20, 2008

(65) Prior Publication Data
US 2010/0297085 A1      Nov. 25, 2010

Related U.S. Application Data

(60) Provisional application No. 60/916,848, filed on May 9, 2007.

(51) Int. Cl.
| | | |
|---|---|---|
| *A01N 63/00* | (2006.01) | |
| *C12N 15/00* | (2006.01) | |
| *C12N 15/09* | (2006.01) | |
| *C12N 15/33* | (2006.01) | |

(52) U.S. Cl.
USPC .......... 424/93.6; 435/320.1; 435/455; 514/44

(58) Field of Classification Search
None
See application file for complete search history.

(56) References Cited

U.S. PATENT DOCUMENTS

| | | | |
|---|---|---|---|
| 5,328,688 A | 7/1994 | Roizman | 424/205.1 |
| 5,585,096 A | 12/1996 | Martuza et al. | 424/93.2 |
| 6,846,670 B2 | 1/2005 | Schwartz et al. | 435/320.1 |
| 2002/0019362 A1 | 2/2002 | Weichselbaum et al. | 514/44 |
| 2006/0188480 A1 | 8/2006 | Coffin et al. | 424/93.2 |
| 2007/0031383 A1 | 2/2007 | Whitley et al. | 424/93.2 |

FOREIGN PATENT DOCUMENTS

WO     WO 98/04726     5/1998

OTHER PUBLICATIONS

Bennett et al, Comparison of safety, delivery, and efficacy of two oncolytic herpes viruses (G207 and NV1020) for peritoneal cancer, Cancer Gene Therapy (2002) 9, 935-945.*

Fu et al, Potent Systemic Antitumor Activity from an Oncolytic Herpes Simplex Virus of Syncytial Phenotype, Cancer Research 62, 2306-2312, Apr. 15, 2002.*

Israyelyan et al, Effective Treatment of Human Breast Tumor in a Mouse Xenograft Model with Herpes Simplex Virus Type 1 Specifying the NV1020 Genomic Deletion and the gBsyn3 Syncytial Mutation Enabling High Viral Replication and Spread in Breast Cancer Cells, Human Gene Therapy 18:457-473 (May 2007).*

Advani, Sunil J. et al., "Replication-competent, Nonneuroinvasive Genetically Engineered Herpes Virus is Highly Effective in the Treatment of Therapy-resistant Experimental Human Tumors," Cancer Res, vol. 59, pp. 2055-2058 (1999).

Andreansky, S. et aL, "Evaluation of Genetically Engineered Herpes Simplex Viruses as Oncolytic Agents for Human Malignant Brain Tumors," Cancer Res, vol. 57, pp. 1502-1509 (1997).

Argnani, R. et al., "Replication-competent Herpes Simplex Vetors: Design and Applications," Gene Therapy, vol. 12, pp. S170-S177 (2005).

Aslakson, Cheryl J. et al., "Selective Events in the Metastatic Process Defined by Analysis of the Sequential Dissemination of Subpopulations of a Mouse Mammary Tumor," Cancer Res, vol. 52, pp. 1399-1405 (1992).

Bennett, Joseph J. et al., "Comparison of Safety, Delivery, and Efficacy of Two Oncolytic Herpes Viruses (G207 and NV1020) for Peritoneal Cancer," Cancer Gene Therapy, vol. 9, pp. 935-945 (2002).

Cozzi, Paul J. et al., "Intravesical Oncolytic Viral Therapy Using Attenuated, Replication-competent, Herpes Simplex Viruses G207 and NV1020 is Effective in the Treatment of Bladder Cancer in an Orthotopic Syngeneic Model," The FASEB Journal, express article 10, 1096 (Published online Mar. 2001).

Cozzi, Paul J. et al., "Oncolytic Viral Gene Therapy for Prostate Cancer Using Two Attenuated, Replication-0Competent, Genetically Engineered Herpes Simplex Viruses," The Prostate, vol. 53, pp. 95-100 (2002).

(Continued)

*Primary Examiner* — Maria Marvich
(74) *Attorney, Agent, or Firm* — John H. Runnels; Bonnie J. Davis

(57) ABSTRACT

A recombinant herpes simplex virus type-1 (HSV-1) has been constructed that carries a deletion of one of the two viral $\gamma_1$ 34.5 genes and other immediate early genes, which render the virus able to selectively replicate in cancer cells but not efficiently replicate in normal cells, and in which specific mutations have been introduced to enable the virus to spread among cancer cells by virus-induced fusion. Specifically, syncytial mutations have been introduced in the genes coding for glycoprotein B and glycoprotein K of the virus, enabling high replication and spread of the virus in cancer cells in the presence of substantially lower amounts of $\gamma_1$ 34.5 protein, which is required for optimum infectious virus produced and virus-induced cell fusion. These altered viruses or the isolated bacterial chromosomes could be used to treat various cancers including breast, liver, colon, and other tissues.

17 Claims, 16 Drawing Sheets

(56) References Cited

OTHER PUBLICATIONS

David, A.T. et al., "The herpes simplex virus type-1 (HSV-1) glycoprotein K (gK) is essential for viral corneal spread and neuroinvasiveness," in press in Current Eye Research (expected May 2008).

Foster, T.P., et al., "Functional and physical interactions of the herpes simplex virus type 1 UL20 membrane protein with glycoprotein K," J of Virol, vol. 82, No. 13, pp. 1-15 (2008).

Foster et al., "The Herpes Simplex Virus Type 1 UL20 Protein Modulates Membrane Fusion Events during Cytoplasmic Virion Morphogenesis and Virus-Induced Cell Fusion," J. of Virology, vol. 78, No. 10, pp. 5347-5357 (2004).

Hoffman, D. et al., "Local and distant immune-mediated contol of colon cancer growth with fusogenic membrane glycoproteins in combination with viral oncolysis," Hum Gene Ther, vol. 18, No. 5, (2007), retraction only.

Hu, J.C. et al., "Oncolytic herpes simplex virus for tumor therapy," Int Rev Neurobiol, vol. 55, pp. 165-184 (2003).

Israyelyan, A.H. et al., "Effective Treatment of Human Breast Tumor in a Mouse Xenograft Model with Herpes Simplex Virus Type 1 Specifying the NV1020 Genomic Deletion and the gBsyn3 Syncytial Mutation Enabling High Viral Replication and Spread in Breast Cancer Cells," Human Gene Therapy, vol. 18, pp. 457-473 (2007).

Israyelyan, Anna et al., "Herpes Simplex Virus Type-1(HSV-I) Oncolytic and Highly Fusogenic Mutants Carrying the NV1020 Genomic Deletion Effectively Inhibit Primary and Metastatic Tumors in Mice," Virology J., vol. 5, No. 68, pp. 1-10 (2008).

Kemeny, N. et al., "Phase I, Open-Label, Dose-Escalating Study of a Genetically Engineered Herpes Simplex Virus NV1020, in Subjects with Metastatic Colorectal Carcinoma to the Liver," Human Gene Therapy, vol. 17, pp. 1214-1224 (2006).

Kramm, C.M. et al., "Therapeutic efficiency and safety of a second-generation replication-conditional HSV1 vector for brain tumor gene therapy," Hum Gene Ther, vol. 8, pp. 2057-2068 (1997).

Li, H. et al., "Induction of Strong Antitumor Immunity by an HSV-2-based Oncolytic Virus in a Murine Mammary Tumor Model," The J. of Gene Med., vol. 9, pp. 161-169 (2007).

Manservigi, Roberto et al., "Cell Fusion Induced by Herpes Simplex Virus is Promoted and Suppressed by Different Viral Glycoproteins," Proc. Natl. Acad. Sci., vol. 74, No. 9, pp. 3913-3917 (1977).

McAuliffe et al., "Effective Treatment of Pancreatic Tumors with Two Multimutated Herpes Simplex Oncolytic Viruses," J. of Gastro. Surg., vol. 4, No. 6, pp. 580-588 (2000).

Meignier, B. et al., "In Vivo Behavior of Genetically Engineered Herpes Simplex Viruses R7017 and R7020: Construction and Evaluation in Rodents," The J. of Infec. Dis., vol. 158, pp. 602-614 (1988).

Meignier, B. et al., In Vivo Behavior of Genetically Engineered Herpes Simplex Viruses R7017 and R7020. II. Studies in Immunocompetent and Immunosuppressed Owl Monkeys (*Aotus trivirgatus*), The J. of Infec. Dis., vol. 162, pp. 313-321 (1990).

Melancon, J.M. et al., "The herpes simplex cirus UL20 protein functions in glycoprotein K (gK) intracellular transport and virus-induced cell fusion are independent of UL20 functions in cytoplasmic virion envelopment," Virology Journal, vol. 4, No. 20, pp. 1-12 (2007).

Miller, Cathie G. et al., "Role of the Immune Response During Neuro-attenuated Herpes Simplex Virus-mediated Tumor Destruction in a Murine Intracranial Melanoma Model," Cancer Res, vol. 60, pp. 5714-5722 (2000).

Miller, Cathie G. et al., "Requirement of an Integrated Immune Response for Successful Neuroattenuated HSV-1 Therapy in an Intracranial Metastatic Melanoma Model," Mol. Ther., vol. 7, No. 6, pp. 741-747 (2003).

Nakamori, Mikihito et al., "Destruction of Nonimmunogenic Mammary Tumor Cells by a Fusogenic Oncolytic Herpes Simplex Virus Induces Potent Antitumor Immunity," Mol. Ther., vol. 9, No. 5, pp. 658-665 (2004).

Pellett, Philip E. et al., "Anatomy of the Herpes Simplex Virus 1 Strain F Glycoprotein B Gene: Primary Sequence and Predicted Protein Structure of the Wild Type and of Monoclonal Antibody-Resistant Mutants," J. of Vir, vol. 53, No. 1, pp. 243-253 (1985).

Pulaski, Beth A. et al., "Reduction of Established Spontaneous Mammary Carcinoma Metastases Following Immunotherapy with Major Histocompatibility Complex Class II and B7.1 Cell-based Tumor Vaccines," Cancer Res, vol. 58, pp. 1486-1493 (1998).

Samoto et al., "A Herpes Simplex Virus Type 1 Mutant with γ34.5 and *LAT* Deletions Effectively Oncolyses Human U87 Glioblastomas in Nude Mice," Neurosurgery, vol. 50, No. 3, pp. 599-606.

Shen, Y. et al., "Herpes simplex virus 1 (HSV-1) for cancer treatment," Cancer Gene Ther., vol. 13, pp. 975-992 (2006).

Thomas, D.L. et al., "HSV-1 Therapy of Primary Tumors Reduces the Number of Metastases in an Immune-Competent Model of Metastatic Breats Cancer," Mol. Ther., vol. 8, No. 4, pp. 543-551 (2003).

Tischer et al., "Two-step Red-mediated Recombination for Versatile High-Efficiency Markerless DNA Manipulation in *Escherichia coli*," Biotechniques, vol. 40, No. 2, pp. 191-196 (2006).

Todo et al., "Oncolytic Virus Therapy Using Genetically Engineered Herpes Simplex Viruses," Human Cell, vol. 15, No. 3, pp. 151-159 (2002).

Todo, Tomoki et al., "Oncolytic Herpes Simplex Virus Vector with Enhanced MHC Class I Presentation and Tumor Cell Killing," PNAS, vol. 98, No. 11, pp. 6396-6401 (2001).

Todo, T. et al., "Systemic antitumor immunity in experimental brain tumor therapy using a multimutated, replication-competent herpes simplex virus," Hum Gene Ther, vol. 10, No. 17, pp. 2741-2755 (1999).

Wong et al., "Angiogenesis Inhibition by an Oncolytic Herpes Virus Expressing Interleukin 12," Clin Cancer Res, vol. 10, pp. 4509-4516 (2004).

Yuhasz et al., "Glycoprotein B is a Specific Determinant of Herpes Simplex Virus Type 1 Neuroinvasiveness," Abstract, Jour. Virology, vol. 67, No. 10, pp. 5948-5954 (1993).

* cited by examiner

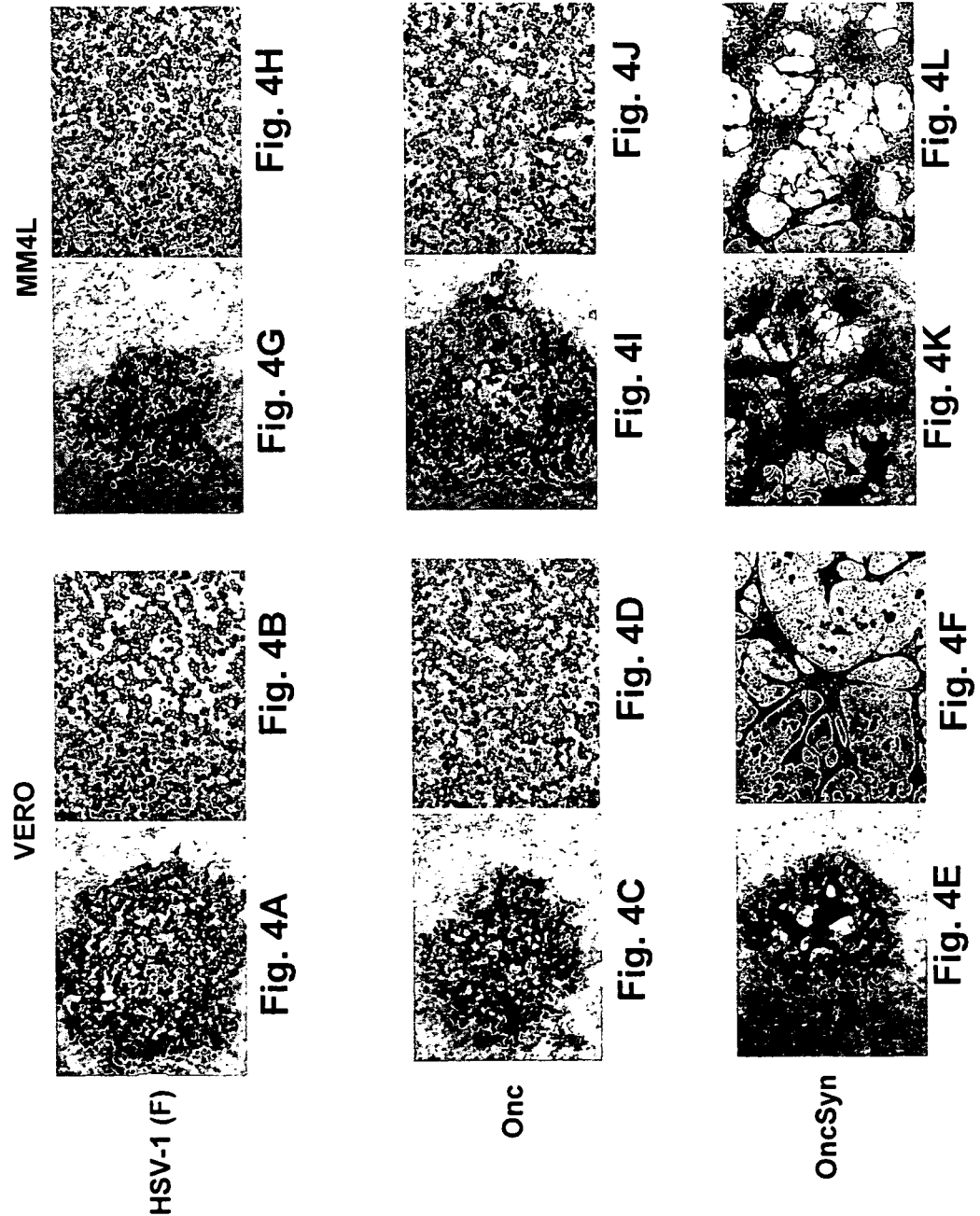

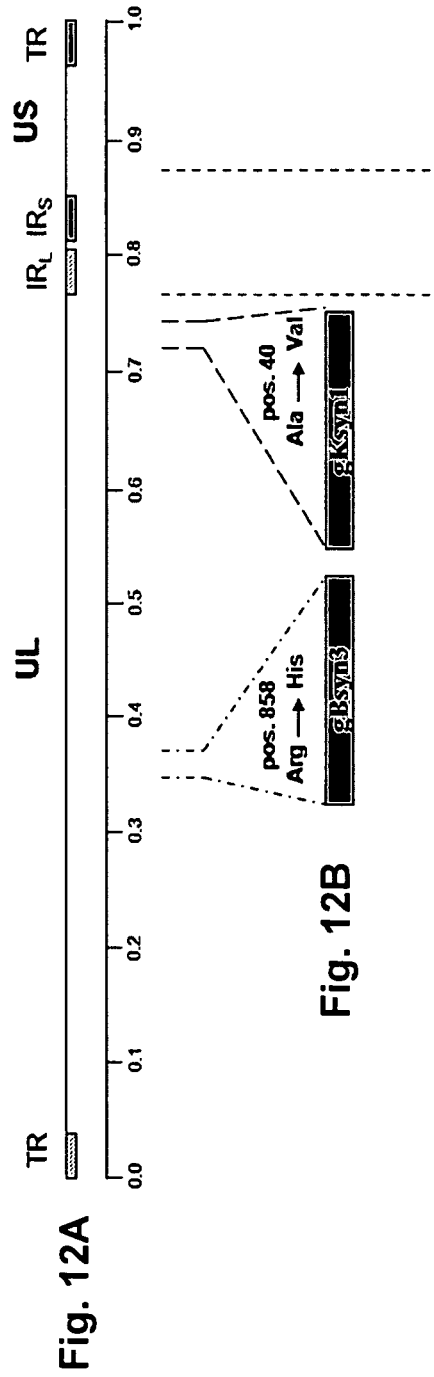
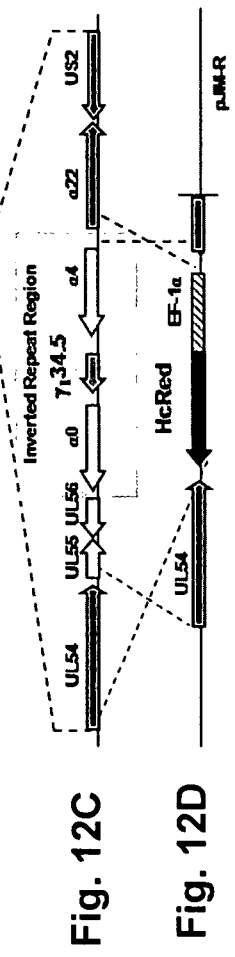
Fig. 12A
Fig. 12B
Fig. 12C
Fig. 12D

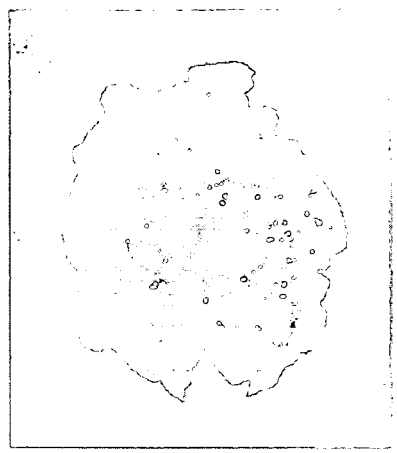
Fig. 16A
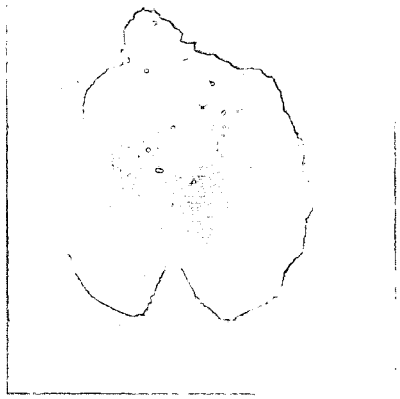
Fig. 16B
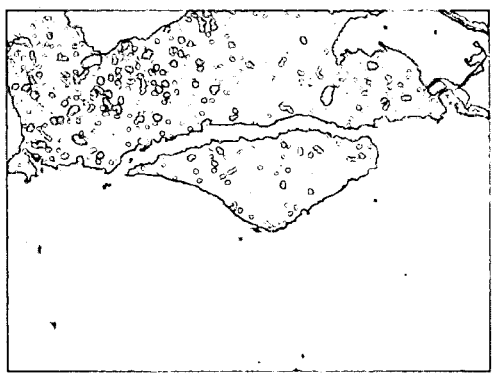
Fig. 16C
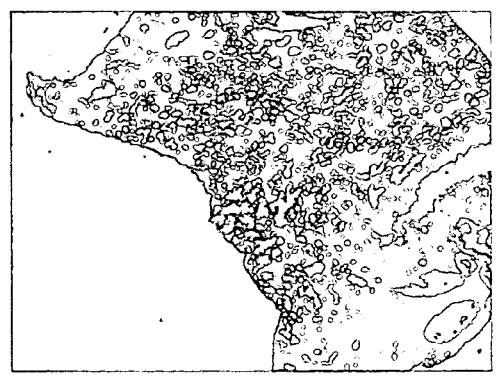
Fig. 16D
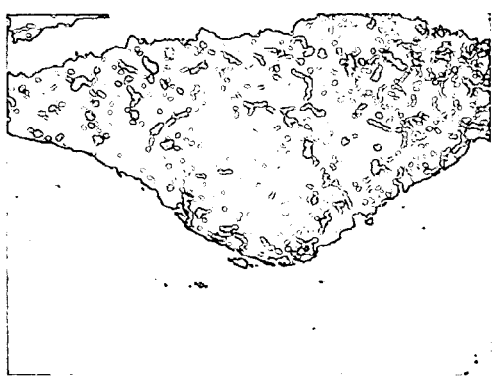
Fig. 16E PBS
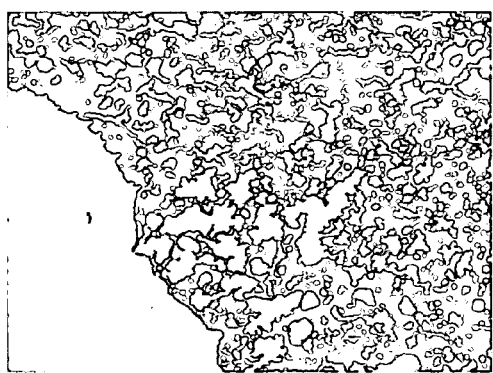
OncdSyn Fig. 16F

SYNTHETIC HERPES SIMPLEX VIRUSES TYPE-1 FOR TREATMENT OF CANCERS

This is the United States national stage of international application PCT/US2008/063206, international filing date May 9, 2008, which claims the benefit of the filing date of provisional U.S. application Ser. No. 60/916,848, filed May 9, 2007, under 35 U.S.C. §119(e).

The development of this invention was partially funded by the Government under grant number RO1 AI43000 from the National Institutes of Health. The Government has certain rights in this invention.

TECHNICAL FIELD

This invention pertains to new oncolytic herpes simplex viruses type-1 (HSV-1) that were engineered to have the ability for high viral replication and spread in cancer cells, but not replicate or spread in normal cells. The new viruses have a single $\gamma_1 34.5$ gene deleted and an additional one or more syncytial mutations within viral genes, e.g., the gBsyn3 mutation within the viral glycoprotein B (gB) or gKsyn1 within the viral glycoprotein K (gK), added to the viral genome.

BACKGROUND ART

Recent advances in molecular virology have enabled investigators to construct viruses that selectively destroy cancer cells (oncolytic virotherapy). Genetically engineered viruses belonging to different viral families have been evaluated for their potential as therapeutic agents in the treatment of malignant tumors. Efficient replication, cell lysis, and spread of herpes simplex viruses (HSV), and their natural broad host range make them attractive candidates as oncolytic viral agents. Furthermore, the recent availability of cloned HSV genomes into bacterial artificial chromosome vectors greatly facilitates the rapid construction of new recombinant viruses carrying multiple transgenes of interest (Jeyaretna and Kuroda, 2007. Tumor treatment with oncolytic HSV has been shown to induce anti-tumor immune responses (Li et al., 2007; Miller and Fraser, 2003; Nakamori et al., 2004; Thomas and Fraser, 2003; Todo et al., 1999). Although the majority of people are seropositive for HSV-1, oncolytic virotherapy with HSV is not limited by pre-existing anti-HSV immunity (Hoffmann, Bayer, and Wildner, 2007; Kemeny et al., 2006), and in at least one example, preexisting immunity to HSV-1 enhanced anti-tumor immune responses (Miller and Fraser, 2000).

Recently, the NV1020 oncolytic herpes simplex virus type-1 (HSV-1) was shown to have significant promise for the treatment of many different types of tumors in preclinical studies in experimental animals as well as in human clinical trials (Cozzi et al., 2002). The main advantage of this virus over other HSV oncolytic viruses is that it expresses one of the two original $\gamma_1 34.5$ genes allowing the virus to replicate more efficiently, while safety is not compromised. The $\gamma_1 34.5$ gene is a major neurovirulence gene and an inhibitor of cellular apoptosis. Deletion of this gene drastically attenuates the virus and restricts viral growth to cancer cells because of their lack of intact apoptotic mechanisms. Preclinical studies in mice as well as phase I/II human trials have revealed that oncolytic HSV-1 viruses having both $\gamma_1 34.5$ genes deleted did not spread efficiently within tumors (Kramm et al., 1997). In contrast, deletion of one of the two $\gamma_1 34.5$ genes drastically attenuated the virus, while allowing improved virus replication and spread in tumor cells (Advani et al., 1999; Meignier, Longnecker, and Roizman, 1988; Meignier et al., 1990). The HSV-1 virus, NV1020, was originally constructed for vaccine purposes and contained HSV-2 viral sequences coding for glycoproteins gD, gG, gI and gE to facilitate production of anti-HSV-2 immune responses, as well as other genetic alternations (Meignier, Longnecker, and Roizman, 1988). A fusogenic oncolytic HSV-1 Synco-2D was reported to elicit anti-tumor immune responses when studied in a similar animal model of mammary carcinoma utilizing 4T1 cells (Nakamori et al., 2004). A strong T-cell response was reported also by an HSV-2 derivative oncolytic virus FusOn-H2 effectively treating primary and metastatic mammary tumors in vivo (Li et al., 2007). A number of different HSV-1 recombinant viruses have been constructed and evaluated for their ability to treat a variety of different cancers in animal models, as well as in human phase I/II clinical trials (Todo, 2002; Hu and Coffin, 2003; Argnani et al., 2005; Shen and Nemunaitis, 2006). The most important modification, which is common to all constructed HSV-1 viruses is the modification/deletion of the $\gamma_1 34.5$ gene, based on the knowledge that $\gamma_1 34.5$ is an important determinant of neurovirulence and an inhibitor of cellular apoptosis.

Although $\gamma_1 34.5$ is non-essential for virus replication, deletion of both copies of the $\gamma_1 34.5$ genes causes substantial reduction in infectious virus production, because the $\gamma_1 34.5$ protein is a structural component of the virion particle and is involved in intracellular glycoprotein transport and cell-surface expression requiring a minimum amount of the protein to be expressed for optimum infectious virus production (Andreansky et al., 1997; Kramm et al., 1997; Todo et al., 2001). In a comparison of the previously constructed R3616 and R7020 that have either both or one of the two $\gamma_1 34.5$ deleted, respectively, R7020 replicated to much higher levels compared to the double-deletion mutant R3616 both in vitro and in vivo (Advani et al., 1999). Furthermore, R7020 replicated preferentially in neoplastic cells and exhibited a remarkable safety profile in extensive rodent and primate studies as well as in human vaccine trials (Meignier et al., 1988; Meignier et al., 1990). R7020 is being currently evaluated in human clinical trials under the name NV1020. Recently, it was shown that NV1020 could be safely administered into the hepatic artery without significant effects on normal liver function in a phase I, open-label, dose-escalating study with subjects having metastatic colorectal carcinoma to the liver (Kemeny et al., 2006). The G207 virus carries a double-deletion of the $\gamma_1 34.5$ gene, as well as a deletion of the UL39 gene coding for the large subunit of the ribonucleotide reductase. (See U.S. Pat. No. 5,585,096). G207 has been extensively studied in animal models and human phase I/II trials. Direct comparison between G207 and NV1020 revealed that NV1020 replicated more efficiently than G207 and exhibited higher oncolytic effectiveness at lower viral doses (McAuliffe et al., 2000; Cozzi et al., 2001; Bennett et al., 2002). Furthermore, G207 was noted to be not only attenuated for pathogenicity, but also for tumor cell killing capability (McAuliffe et al., 2000; Cozzi et al., 2001; Bennett et al., 2002).

HSV can be transmitted from cell-to-cell by causing limited amounts of virus-induced cell fusion, thus avoiding the extracellular environment. Specific mutations within viral glycoproteins are known to greatly enhance virus-induced cell fusion. Specifically, syncytial mutations that cause extensive virus-induced cell fusion can arise in at least two of the glycoprotein genes: the UL27gene, encoding glycoprotein B (gB) (Bzik et al., 1984a; Bzik et al., 1984b; Pellett et al., 1985; Manservigi, Spear, and Buchan, 1977), and the UL53 gene, coding for glycoprotein K (gK) (Bond and Person, 1984; Debroy, Pederson, and Person, 1985). Glycoprotein gK has been shown to function as a heterodimer with the UL20 viral protein and the UL20/gK heterodimer is necessary for virus-induced cell fusion (Foster et al., 2004; Melancon et al., 2007).

Breast cancer is the most common cancer among women, excluding cancers of the skin, accounting for nearly 1 in 3 cancers diagnosed in US women. In western countries breast cancer is the second leading cause of cancer death in women and is associated with high morbidity and mortality. A new and promising strategy for cancer therapy is the use of modified viruses that have been engineered to selectively replicate within cancer cells (oncolytic virotherapy). A number of viruses have been explored as tumor-selective replicating vectors, including adenovirus, herpes simplex virus type-1 (HSV-1), vaccinia virus, reovirus, Newcastle disease virus, vesicular stomatitis virus, measles virus, poliovirus and West Nile virus. Multiple murine tumor models have been used as preclinical settings for therapeutic purposes. The 4T1 mammary carcinoma model has several distinct advantages to be used as such model. It is regarded as a highly physiological, clinically-relevant mouse model that closely resembles stage 1V human breast cancer in its properties (Aslakson and Miller, 1992). 4T1 cells are considered to be very weakly immunogenic (relative antigenic strength is less than 0.01 with 9.9 being the most immunogenic), and they spontaneously metastasize to distal parts of the body (Aslakson and Miller, 1992; Pulaski and Ostrand-Rosenberg, 1998).

U.S. Pat. No. 5,328,688 discloses a recombinant herpes simplex virus vaccine based on the making the virus avirulent by prevention of expression of the $\gamma_1$ 34.5 gene.

International Publication No. WO 98/04726 discloses a herpes simplex virus strain that is disabled by inactivating both ICP34.5 and ICP27 genes for use as a gene delivery vector.

U.S. Patent Application Publication No. 2002/0019362 discloses treatment of cancers with a herpes simplex virus that has an alteration in the $\gamma_1$ 34.5 gene.

U.S. Pat. No. 6,846,670 discloses a genetically engineered herpes virus vector for treatment of cardiovascular disease that is modified by lacking a $\gamma_1$ 34.5 gene and operably comprises a heterologous nucleic acid.

U.S. Patent Application Publication No. 2007/0031383 discloses a recombinant herpes simplex virus expressing only a single $\gamma_1$ 34.5 gene and an expressible cytokine-encoding DNA.

DISCLOSURE OF INVENTION

I have constructed a recombinant herpes simplex virus type-1 (HSV-1) that carries a deletion of one of the two viral $\gamma_1$ 34.5 genes and other immediate early genes, which render the virus able to selectively replicate in cancer cells but not efficiently replicate in normal cells. In addition, specific mutations have been introduced within viral genes to enable the virus to spread among cancer cells by virus-induced fusion. Specifically, syncytial mutations have been introduced in the genes coding for glycoprotein B and glycoprotein K of the virus, which enabled high replication and spread of the virus in cancer cells. Other known syncytial mutations could also be introduced that would render the virus able to cause extensive virus-induced cell fusion. The ability of these viruses to replicate to relatively high titers and cause virus-induced cell fusion depends on the limited expression of the remaining $\gamma_1$ 34.5 gene that has not been deleted. These altered viruses could be used to treat various cancers including breast, liver, colon, and other tissues by direct administration of the altered virus to tumors.

BRIEF DESCRIPTION OF THE DRAWINGS

FIG. 1 illustrates a schematic representation of the strategy used to generate the HSV-1Onc (Onc) and HSV-1OncSyn (OncSyn) viruses and PCR-based molecular characterization of the constructed viruses.

FIG. 4 illustrates the plaque phenotypes of HSV-1(F), Onc, and OncSyn viruses. The plaque phenotypes of HSV-1(F), Onc, and OncSyn viruses were observed on Vero (A to F) and MM4L (G to L) cells. Near confluent cell monolayers were infected with wild-type HSV-1(F) derived from pYEbac102 (A, B, G, and H), Onc (C, D, I, and J), and OncSyn (E, F, K, and L) at low (A, C, E, G, I, and K) and high (B, D, F, H, J, and L) MOI. Viral plaques were visualized at 48 hr post infection by immunohistochemistry.

FIG. 12 is a schematic representation of the genomic structures of the oncolytic recombinant viruses OncSyn and OncdSyn. The top line, FIG. 12A, represents the prototypic arrangement of the HSV-1 genome with the unique long (UL) and unique short (US) regions flanked by the terminal repeat (TR) and internal repeat (IR) regions. FIG. 12B shows the approximate locations of the gB and gK genes. FIG. 12C is an expansion of the inverted repeat region showing the approximate locations of UL54, UL55, UL56, α0, γ$_1$34.5, α4, α22 and US2 genes. FIG. 12D is a schematic of the DNA fragment cloned into plasmid pJM-R, which was used for insertion of the HcRed gene cassette into the viral genome in place of the NV1020 genomic deletion as described in Materials and Methods.

FIG. 15 illustrates the intra-tumor treatment with OncSyn and OncdSyn viruses.

FIG. 16 illustrates the therapeutic effect of OncdSyn virus on lung metastases. In FIGS. 16A and 16B, the gross appearance of excised lungs of representative mice from PBS control and OncdSyn treated groups is pictures. In FIGS. 16C-16F, representative sections of lung tissues stained with H&E are shown after treatment with PBS (FIGS. 16C and 16D) or OncdSyn (FIGS. 16E and 16F) and examined at 40× (FIGS. 16C and 16E) and 100× (FIGS. 16D and 16F) magnifications.

MODES FOR CARRYING OUT THE INVENTION

Figures 1A, 1B, 1C, 1D:
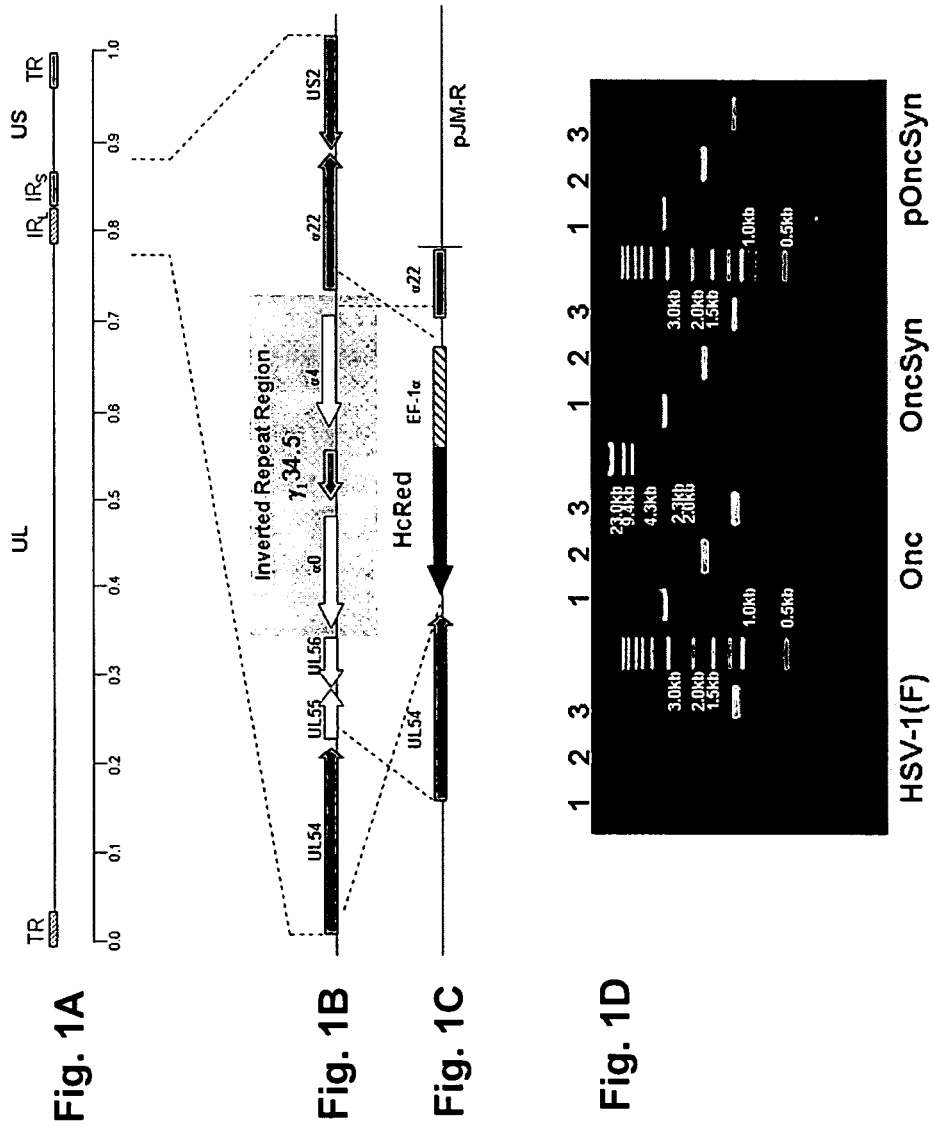
FIG. 1A, the top line, represents the prototypic arrangement of the HSV-1 genome with the unique long (UL) and unique short (US) regions flanked by the terminal repeat (TR) and internal repeat (IR) regions.
FIG. 1B shows the expanded inverted repeat region with approximate locations of UL54, UL55, UL56, 2 0, 41 34.5, 2 4, 2 22 and US2 genes.
FIG. 1C is a schematic of the DNA fragment cloned into plasmid pJM-R, which was used for insertion of the HcRed gene cassette into the viral genome.
FIG. 1D shows the results of a diagnostic PCR test using primers A and B flanking the insertion site to confirm the presence of the inserted gene cassette expressing the HcRed gene in place of the deleted genomic region in Onc (lane 1), OncSyn (lane 1), and pOncSyn (lane 1), but not in HSV-1(F) (lane 1).

Two new prototypic HSV-1 recombinant viruses, HSV-1OncSyn (OncSyn) and HSV-1OncdSyn (OncdSyn) have been engineered. The OncSyn virus has one of the two γ$_1$ 34.5 genes as well as adjacent sequences deleted, and carries a syncytial mutation within the UL27gene encoding gB. In addition, one of the two genomic regions coding for the latency associated transcripts (LAT) was deleted. The OncSyn virus replicated efficiently in human breast cancer cells in cell culture yielding higher viral titers than either the wild-type HSV-1(F) or parental Onc viruses. Viral glycoproteins including gB were efficiently expressed on cell surfaces indicating that the remaining single γ$_1$ 34.5 gene adequately supported intracellular glycoprotein transport and cell-surface expression. Importantly, the OncSyn virus spread substantially better in breast cancer cells than in Vero cells producing large syncytial plaques. Intra-tumor injections of the OncSyn virus within xenografts of human breast cancer cells injected into nude mice showed remarkable reduction of tumor size, and extensive necrosis of tumor cells. The results show that the constructed OncSyn virus can effectively kill tumor cells both in vitro and in vivo. Intratumoral delivery of the OncSyn virus produced a significant therapeutic effect as evidenced by the drastic reduction of treated tumors. The OncSyn virus was able to infect, replicate, and effectively fuse and destroy the human breast cancer cells in vitro and in vivo. Overall, results confirm the safety, efficacy, and potential of the OncSyn virotherapy for treatment of breast cancer.

In addition, a new virus was constructed by introducing the syncytial mutation gKsyn1 into the OncSyn viral genome cloned into a bacterial artificial chromosome using double-red mutagenesis in *E. coli* to produce the OncdSyn virus carrying syncytial mutations in both gB(syn3) and gK(syn1). The OncdSyn virus caused extensive virus-induced cell fusion in cell culture. The oncolytic potential of the OncSyn and OncdSyn viruses was tested in the highly metastatic syngeneic mouse model system, which utilizes 4T1 murine mammary cancer cells implanted within the interscapular region of Balb/c mice. Mice were given three consecutive intratumor injections of OncSyn, OncdSyn, or phosphate buffered saline every four days. Both OncSyn and OncdSyn virus injections resulted in significant reduction of tumor sizes (p<0.05) compared to control tumors. Virus treated mice but not controls showed a marked reduction of metastatic foci in lungs and internal organs. These results show that the attenuated, but highly fusogenic OncSyn and OncdSyn viruses can effectively reduce primary and metastatic breast tumors in immunocompetent mice. Glycoprotein K has been shown to be important in virus transmission to neurons (data not shown; David et al., Current Eye Research, In press). Certain mutations in gK and UL20 genes can affect the interaction of UL20 and gK proteins in such a way as to reduce infectious virus production and neuronal transmission without affecting the ability of gK and UL20 proteins to facilitate virus-induced cell fusion (i.e. deletion of the terminal six amino acids of UL20 protein). Therefore, additional mutations in gK and UL20p can be combined with syncytial mutations in gK, gB, etc., to produce a highly attenuated virus with impaired ability to be transmitted to neurons, where the virus normally establishes latency. (data not shown) Other genomic additions can be made to the OncSyn or OncdSyn viruses that will increase the oncolytic therapeutic value of the virus. (Vaha-Koskela et al., 2007) For example, the vectors have been used to produce immunomodulatory molecules, for example, cytokines or other proteins, known to stimulate immune recognition (e.g., interleukins, granulocyte macrophase-colony stimulus factor). (Mullen et al., 2004; Liu et al., 2003). Other proteins that could be delivered by viruses are prodrug conversion enzymes (e.g., yeast cytosine deaminanse (Nakamura, 2001), and angiogenesis inhibitors (e.g., endostatin) (Mullen et al., 2004).

The OncSyn virus was re-isolated as a bacterial artificial chromosome (pOncSyn), which will enable the rapid construction of additional viruses that may exhibit increased efficacies in breast cancer treatments. Using similar techniques, the OncdSyn virus will be re-isolated as a bacterial artificial chromosome (pOncdSyn). The availability of both OncSyn and OncdSyn viruses as bacterial artificial chromosomes will enable the generation of additional recombinant viruses that carry multiple anti-tumor and immunomodulatory transgenes. Potential future modifications may include placing the remaining $\gamma_1$ 34.5 gene under a breast tumor-specific promoter control, as well as including one or more transgenes that can enhance the oncolytic properties of the virus including genes that express cytolytic peptides, genes that express immunomodulatory proteins, genes that express prodrug converting enzymes, genes that express angiogenesis inhibitors, genes that express siRNAs targeting viral oncogenes, etc. In this regard, the large deletion of the virus and its availability as a cloned genome into a bacterial artificial chromosome (bac) vector renders the rapid incorporation of multiple gene cassettes feasible without being severely limited by viral genome packaging restrictions.

Other mutations in the genes that code for the fusogenic glycoproteins (e.g., gB or gK) or in the UL20 and UL24 genes are known to have syncytial mutations, each of which can be combined with the HSV-1 viral genome that lacks only a single $\gamma_1$ 34.5 gene to form an effective oncolytic virus. Syncytial mutations in UL53, the gene that codes for gK, include mutations identified in a variety of syncytial mutants including syn8, syn30, syn31, syn32, syn102, syn103, syn105 (Dolter et al. J. Virol. 68:8277-8281, 1994). Syncytial mutations in UL27, the gene that codes for gB, include truncations of the carboxyl terminus (Fan et al, J. Virol. 76:9271-83, 2002; Baghian et. Al. J. Virol. 67: 2396-2401, 1993), as well as other syncytial mutations (Ruell et al, Virology 346: 229-37, 2006; Gage et al. J. Virol. 67: 2191-201, 1993). Mutations in UL20 include truncations, alanine insertions and single amino acid changes (Rajcani J and Voivodova A. Acta Virol. 42: 103-18, 1998; Melancon et al, J Virol. 78:7329-43, 2004). Mutations in UL24 include deletions, truncations and single amino acid changes (Rajcani J and Voivodova A. Acta Virol. 42: 103-18, 1998). (Also new reference, Foster et al 2008, In press). Because of the strict requirement for gK to interact with the UL20 protein, certain mutations in the UL20 gene can also cause virus-induced cell fusion (Melancon et al, 2008 Virology Journal, In press).

Examples of uses of the new viruses for treatment include treating non-human animals and humans suffering from tumors (neoplasms). Preferentially the treatment would be by direct intratumoral injection, or intravascular injection proximal to the tumor. A typical composition for such injection would comprise the virus and a pharmaceutically acceptable vehicle, which could either include aqueous and non-aqueous solvents. Aqueous vehicles include water, saline solutions, sugar solutions (e.g., dextrose), and other non-toxic salts, preservatives, buffers and the like. Non-aqueous solvents include propylene glycol, polyethylene glycol, vegetable oils, and other non-toxic organic solutions.

The amount of virus to be administered, both in terms of the number of treatments and the dose for each treatment, will depend on the size and health of the subject and the type and location of the tumor. Oncolytic viral therapy has been used for many mammalian solid tumors, for example, breast tumors, pancreatic tumors, prostate tumors, brain tumors, peritoneal tumors, and colorectal tumors. (Cross et al., 2006).

This invention is directed to recombinant herpes simplex virus whose chromosome concurrently lacks the coding sequence for a single neurovirulence gene, $\gamma_1$ 34.5, and comprises a mutated coding sequence in a gene that codes for either a fusogenic protein or a protein that regulated virus-induced cell fusion, such that the mutated coded sequence incorporated into the viral chromosome increases the ability of the virus to promote virus-induced cell fusion. The term "mutated coded sequence" refers to change in the nucleotide sequence of a viral gene such that the resulting protein has a change in one to five amino acids, or that deletes one to five amino acids. Many of the known syntial mutations result in a single amino acid change; however, syntial mutations for both gK and UL20 are known that delete certain amino acids from either the carboxyl or amino terminus. OncSyn is an example of a virus with a deleted $\gamma_1$ 34.5 gene and the syntial mutation, gBsyn3, in the UL27gene. OncdSyn is an example of a virus with a deleted $\gamma_1$ 34.5 gene and two syntial mutations, gBsyn3 in the UL27gene and gKsyn1 in the UL53 gene. Both viruses were shown to have an increase in virus-induced cell fusion due to the mutations. Both viruses were also shown to have therapeutic effects against a mouse tumor.

The invention is also directed to artificial bacterial chromosomes that contain the entire viral genome of a recombinant herpes simplex virus with a deletion of the one of the neurovirulence genes, $\gamma_1$ 34.5, and with at least one syntial mutation in a gene that codes for a fusogenic protein or a protein that regulates virus-induced cell fusion, such that the ability of the virus to promote virus-induced cell fusion is enhanced, for example, the genome of OncSyn or OncdSyn.

The invention is also directed to recombinant herpes simplex virus with a deletion of the one of the neurovirulence genes, $\gamma_1$ 34.5, and with at least one syntial mutation in a gene that codes for a fusogenic protein or a protein that regulates virus-induced cell fusion, such that the ability of the virus to promote virus-induced cell fusion is enhanced, and additionally wherein the viral genome contains a gene cassette of a regulatory promoter and a protein that would increase the oncolytic effect of the virus or a siRNA that would target viral oncogenes.

The invention is also directed to methods of treating neoplastic diseases or tumors by administering the recombinant herpes simplex viruses as described above to patients with such diseases or tumors.

EXAMPLE 1

The OncSyn Virus

Materials and Methods

Cells, viruses and plasmids. African green monkey kidney (Vero) cells, human breast cancer cells (Hs578T) (Hackett et al., 1977), and mouse mammary tumor cells (4T1) (Aslakson and Miller, 1992) were obtained from the American Type Culture Collection (Manassas, Va.). The human breast adenocarcinoma line MDA-MB-435-luc expressing luciferase (MM4L) (Leuschner et al., 2003) was kindly provided by Dr. C. Leuschner (Pennington Biomedical Research Center, Baton Rouge, La.). Vero and Hs578T cells were maintained in Dulbecco's modified Eagle's medium (Gibco-BRL; Grand Island, N.Y.), supplemented with 10% fetal calf serum and antibiotics. 4T1 cells were maintained in RPMI 1640 medium (Hyclone, Logan, Utah) containing 10% FBS. The cultures were maintained at 37° C. in a humidified atmosphere of 5% $CO_2$/95% air. MM4L cells were cultured with Leibovitz's L-15 medium (Hyclone, Logan, Utah) containing 10% FBS. These cells were cultured in tightly closed flasks in a 37° C. incubator. The plasmid pYEbac102 containing the HSV-1(F) (Tanaka et al., 2003) viral genome was kindly provided by Dr. Y. Kawaguchi (Tokyo Medical and Dental University, Tokyo, Japan). The plasmid pRB3410 was kindly provided by Dr B. Roizman (University of Chicago, Chicago, Ill.) (Meignier et al., 1988). All viruses were routinely grown and titrated in Vero cells. The plasmid encoding red fluorescent protein (pHcRed1-N1) was obtained from BD Biosciences, Clontech (Palo Alto, Calif.). The pEF6/V5-His-TOPO plasmid was obtained from Invitrogen (Carlsbad, Calif.).

Construction and genomic characterization of recombinant viruses HSV-1Onc (Onc) and HSV-1OncSyn (OncSyn). The red fluorescent protein (RFP) gene was PCR-amplified from plasmid pHcRed1-N1 and cloned into the plasmid pEF6/V5-HisTOPO. Subsequently, the RFP gene under the elongation factor 1-alpha (EF-1α) promoter was cloned into the pRB3410 XbaI site producing plasmid pJM-R. In this plasmid the RFP gene cassette interrupts the viral sequence creating two 1838 and 2300 by viral DNA flanking segments to facilitate homologous recombination with the viral genome.

Vero cells were transfected with pJM-R and twenty-four hours post-transfection cells were infected with the pYEbac102-derived virus. Red virus plaques formed on Vero cells were collected and sequentially plaque-purified at least six times. The resultant virus was named HSV-1Onc (Onc). An HSV-1(F) isolate constructed in this laboratory to contain a single amino acid change in glycoprotein B (gBsyn3) (Melancon et al., 2005) was used in co-infection experiments with the Onc virus to isolate a virus that contained both the Onc and gBsyn3 mutations. The resultant virus (OncSyn) was plaque purified at least six times. The targeted deletions of the $\gamma_1$ 34.5 gene and neighboring sequences, including the UL56, α0, and α4 genes, and the concomitant insertion of the HcRed gene cassette were confirmed by restriction endonuclease analysis, diagnostic PCR and sequencing. The OncSyn viral genome was recovered as a bacterial artificial chromosome into E coli using similar methodologies described in the isolation of the pYEbac102 (Tanaka et al., 2003). The original pYEbac102 containing the HSV-1(F) genome was compared to pOncSyn containing the HSV-1(F) OncSyn genome via restriction EcoRI endonuclease analysis. For diagnostic PCR, primers F-UL54end (A: 5'-AGGAGTGTT CGA GTCGT-GTCT-3' (SEQ ID NO: 1)) and R-ICP4prom (B: 5'-TGGGAC TATATGAGCCCGAG-3' (SEQ ID NO: 2)) flanking the insertion site were used to confirm the presence of the insertion in place of the deleted genomic region. Primer A mentioned above and primer R-HcRed (C: 5'-CCTGCTGAAG GAGAGTATGCG-3' (SEQ ID NO: 3)) were used to confirm the presence of the inserted HcRed gene cassette. Primers F-gK (D: 5'-ATGCTCGCCGTCCGTTCCCTGC-3' (SEQ ID NO: 4)) and R-gK (E: 5'-ATCAAACAG GCGCCTCTG-GATC-3' (SEQ ID NO: 5)) were used to amplify the UL53 gene as a positive control.

Phenotypic characterization and replication kinetics of Onc and OncSyn viruses. Cells (both Vero and the tumor cell lines) were seeded into 6-well plates and infected the following day (when they reached approximately 95% confluency) with either Onc or OncSyn at a dose ranging from 0.1 to 0.001 PFU/cell (plaque forming units per cell). Cells were cultured in a maintenance medium (containing 1% FBS) and were left for 2 days to allow for the plaques and the cell fusion to develop. Photographs of the infected cells were taken using a fluorescent microscope. For plaque morphology visualized by immunohistochemistry, Vero cells were infected at MOIs (Multiplicity of Infection=ratio of infectious virus particles to cells) of 0.01 (low) and 1 (high) with HSV-1 (F), Onc and OncSyn viruses and visualized by immunohistochemistry at 48 hours post-infection (h.p.i.) with horseradish peroxidase-conjugated anti-HSV antibodies (Dako, Carpinteri, Calif.) and Novared (VectorLabs, Burlingame, Calif.) substrate development. To determine the replication kinetics of the viruses, analysis of one-step growth kinetics was employed as described previously (Foster et al., 2001b; Foster et al., 2003). Briefly, each virus at an MOI of 2 was adsorbed to approximately $6 \times 10^5$ Vero or MM4L cells at 4° C. for 1 h. Thereafter, warm medium was added, and virus was allowed to penetrate for 2 h at 37° C. Any remaining extracellular virus was inactivated by low-pH treatment with phosphate buffered saline at pH 3.0. Cells and supernatants were harvested immediately thereafter (0 h) or after 6, 12, 18, 24, or 30 h of incubation at 37° C. Virus titers were determined by endpoint titration of virus stocks on Vero cells.

FACS analysis. Monoclonal antibodies against glycoproteins gB (HSB1), gC (HSC1), and gH (52-S) were used as described previously (Cavalcoli et al., 1993). A polyclonal mouse anti-gD antibody was used as described previously (Baghian et al., 2002). Monolayers of Vero cells were infected with Onc and OncSyn viruses. Cells were harvested 14 h after infection and washed twice with phosphate-buffered saline (PBS) containing 2% fetal bovine serum and concentrated by centrifugation. The procedures were performed as described previously (Baghian et al., 1992). Cell pellets were resuspended in 100 µl of the appropriate antibody dilution, and incubated at 4° C. for 1 h. Unbound antibody was removed by washing the cells twice with PBS. Pellets of cells were incubated for 1 h with 100 µl of the secondary antibody, a fluorescein-conjugated goat anti-mouse antibody (ICN Pharmaceuticals, Inc., Aurora, Ohio), diluted 1:50 in PBS containing 10% heat inactivated goat serum and then incubated for an additional 1 h at 4° C. The cells were washed twice as described above and analyzed immediately. A standard fluorescence-activated cell sorter (FACS) analysis was carried out with a FACScan (BD Biosciences, San Jose, Calif.). Images of the FACS data were generated with Cell Quest software (BD Biosciences, San Jose, Calif.).

Animal experiments. Female athymic nude mice (6 weeks of age) (Charles River Laboratories, Inc, Wilmington, Mass.) were housed in autoclaved cages with a high efficiency filter-tops and autoclaved bedding. The animal room was kept at 25° C. with a 12 hour light-dark cycle. At 6-7 weeks of age the animals (21-23 g body weight) were subcutaneously implanted with $1 \times 10^6$ MM4L cells suspended in 0.1 ml of PBS and 0.3 ml of phenol red free Matrigel (Collaborative Biomedical Products, Beckton Dickinson Labware, Bedford, Mass.) using a 27 gauge needle (Wilson and Sinha, 1997; Koshizuka et al., 1999). Body weights were determined weekly, and tumor size was monitored beginning 16 days after tumor inoculation by measuring with a digital micro-caliper. Tumor volumes were calculated using the following formula: volume=(length×width×height)/2. At an average tumor volume of approximately 70-80 mm$^3$ (day 22 after tumor cell inoculation), the 72 experimental animals were randomized into 3 groups with two subgroups each using a randomization plan developed by Dr. Gerard E. Dallal and available online (Randomization.com). The 3 groups of mice (24 animals per group) received 3 intra-tumoral injections of the OncSyn viral particles, PBS, or heat and UV inactivated OncSyn. Injections per tumor contained $2 \times 10^6$ viruses per injection in 250 µl volume, 250 µl of PBS, or 250 µl of heat and UV inactivated OncSyn. The tumors from half of the animals from each group (one subgroup) were visualized by a chemiluminscence in vivo imaging system IVIS 50 (Xenogen, Alameda, Calif.). Mice were humanely euthanized five days after the last injection of the first round. The remaining animals received the second round of injections, again consisting of three consecutive injections of OncSyn, PBS, or heat and UV inactivated OncSyn. In vivo imaging was performed and mice were humanely euthanized 5 days after the last injection. Animals were given a necropsy examination after either the first or second round of injections. The weights of freshly excised tumors were determined. The primary tumor site, all lung lobes, liver, spleen, and kidneys from each animal were fixed in 10% neutral buffered formalin, trimmed, processed routinely, stained with hematoxylin and eosin (H and E) and evaluated by light microscopy. In addition to conventional evaluation of the histological slides for pathological changes, severity of tumor cell necrosis was determined on a 0 to 4 score scale (0=no necrosis, 1=1%-25% necrosis, 2=26%-50% necrosis, 3=51%-75% necrosis, and 4≥76% necrosis).

Chemiluminescence in vivo imaging of live animals was performed on the scheduled days of necropsies. Specifically, tumors of 36 animals, 12 from each group, were visualized by chemiluminescence imaging, and mice were necropsied after receiving the first round of injections. The remainder of the mice were imaged and necropsied after receiving the second round of injections using a whole animal chemiluminescence in vivo imager. Mice were injected with 150 mg/kg D-luciferin intraperitoneally (approximately 100 microliters). The luciferin was diluted with phosphate-buffered saline to a final concentration of 30 mg/ml. After 15-20 minutes to allow the luciferin to be absorbed and circulate, mice were anesthetized with Avertin (2,2,2 tribromo-ethanol) at 0.4-0.6 mg/gm intraperitoneally. After 3 minutes, to allow for the Avertin to take effect, the mice were imaged for 5-7 minutes. The animal studies were approved by the local institutional animal care and use committee (IACUC).

Statistical methods and analyses. The SAS® statistical package (Version 9.1.3) was used for all the analyses of the in vivo studies. Distributions were examined for normality using the UNIVARIATE procedure with a Shapiro-Wilk test of normality. For the repeated measures part of the analyses of tumor volumes and tumor weights, the GLM procedure was used to conduct a repeated measures design analyzed as a split-plot arrangement of treatments with TREATMENT (inactivated OncSyn, PBS, and OncSyn) and MOUSE within TREATMENT as main plot factors. Subplot factors included PERIOD (days of measurements) and TREATMENT by PERIOD interaction. When overall analyses determined significance ($p<0.05$), Tukey's HSD test was used to examine pairwise differences for main effects, and pairwise comparisons of least square means with regard to interaction effects were examined with preplanned t-tests. A one-way analysis of variance was used to analyze the $\log_e$-transformed chemiluminescence imaging data for each separate necropsy group. Necropsy data (excised tumor weights) were analyzed as a one-way analysis of variance for TREATMENT effects with Tukey's HSD test used for post hoc pairwise comparisons of individual effects in the model ($p<0.05$). Necrosis scores were analyzed with the Kruskal-Wallis test to determine the effect of treatment on necrosis scores. Potential differences in animal weights were analyzed with a one-way analysis of variance. Pearson correlation coefficients within each injection and treatment were used to examine linear relationships among animal weights, tumor weights and tumor volumes. In addition, when necrosis scores were included in the variable list a Spearman correlation coefficient was used. Animal weights within each group were also examined over time with Pearson correlations.

EXAMPLE 2

OncSyn

Construction and Characterization of Oncolytic HSV-1 Mutant Viruses Onc and OncSyn To attenuate HSV-1(F), but at the same time allow for efficient replication within tumor cells, a strategy was designed to delete a large portion of the HSV-1(F) genome containing one of the two alleles of the immediate early genes α4 and α0, as well as the virulence gene $\gamma_1$ 34.5. The strategy was similar to the one previously used for the construction of the R7020 recombinant virus, in which an approximately 16 Kbp genomic region encompassing the UL56, α0, $\gamma_1$ 34.5, and α4 genes was deleted. The deleted genomic region of the R7020 was replaced with a herpes simplex virus type-2 (HSV-2) DNA sequences coding for viral glycoproteins gD, gG, gI and a portion of gE, as well as a gene cassette expressing the viral thymidine kinase (TK) gene under the α4 promoter control (Meignier et al., 1988). In contrast to the R7020 recombinant virus, the Onc virus was designed to contain a gene cassette coding for the enhanced red fluorescence protein inserted within the deleted genomic region, while the viral TK gene remained intact in its natural genomic location (FIG. 1).

FIG. 1 illustrates the schematic representation of the strategy used to generate the HSV-1Onc (Onc) and HSV-1OncSyn (OncSyn) viruses and PCR-based molecular characterization of the constructed viruses. FIG. 1A, the top line, represents the prototypic arrangement of the HSV-1 genome with the unique long (UL) and unique short (US) regions flanked by the terminal repeat (TR) and internal repeat (IR) regions. FIG. 1B shows an expanded inverted repeat region with approximate locations of UL54, UL55, UL56, α0, $\gamma_1$ 34.5, α4, α22 and US2 genes. FIG. 1C is a schematic of the DNA fragment cloned into plasmid pJM-R, which was used for insertion of the HcRed gene cassette into the viral genome. In this plasmid, the HcRed gene cassette was inserted in place of the $\gamma_1$ 34.5 gene and adjacent sequences, while other flanking sequences were retained to facilitate homologous recombination with the viral genome. FIG. 1D shows the results of a diagnostic PCR test using primers A and B flanking the insertion site to confirm the presence of the inserted gene cassette expressing the HcRed gene in place of the deleted genomic region in Onc (lane 1), OncSyn (lane 1), and pOncSyn (lane 1), but not in HSV-1(F) (lane 1). The fragment sizes of the DNA ladder markers are denoted in kilobases (kb). Primers A and C (insertion specific primer) were used to verify the specific presence of the HcRed gene in Onc (lane 1), OncSyn (lane 1), and pOncSyn (lane 1), but not in HSV-1(F) (lane 1). Primers D and E were used to amplify the UL53 gene to serve as a PCR positive control (see Example 1 above) (lane 3 for HSV-1(F), Onc, OncSyn, and pOncSyn).

Specifically, plasmid pRB3410 containing an approximately 16 kilobase pair (Kbp) fragment spanning the viral genomic site containing the $\gamma_1$ 34.5 gene was modified to include the HcRed gene cassette (RFP gene under the control of the EF-1$\alpha$) immediately flanked by the UL54 and a 22 genes (FIG. 1C; see Example 1 above). Homologous recombination between the transfer plasmid and the viral genome in a transfection followed by infection experiment resulted in viral plaques emitting red fluorescence when observed under a fluorescence microscope.

To facilitate virus spread via virus-induced cell fusion, the OncSyn virus was isolated after double-infection of Vero cells with Onc and a HSV-1(F) laboratory strain specifying the gBsyn3 mutation. Individual viral plaques exhibiting the syncytial phenotype and emitting red fluorescence were isolated and extensively plaque-purified. Individual viruses were plaque-purified and the targeted deletion/insertion was verified by DNA sequencing of the entire genomic region bracketing the deletion/insertion, as well as by PCR analyses (FIG. 1D). The presence of the gBsyn3 mutation was verified by DNA sequencing. Primers A and B (see Example 1 above) flanking the insertion site amplified the predicted 3,126-bp DNA fragment from Onc (lane 1), OncSyn (lane 1), and pOncSyn (lane 1), which contain the inserted gene cassette. As expected, the HSV-1 (F) wild-type viral DNA produced no amplified product (lane 1). Amplification using primers A and C produced the predicted 1,693-bp DNA fragment confirming the presence of the HcRed gene cassette (lane 2 for Onc, OncSyn, and pOncSyn). Primers D and E amplified the predicted 1060-bp UL53 DNA fragment from all four constructs, since they all contain the wild-type UL53 gene (lane 3).

Figure 2:
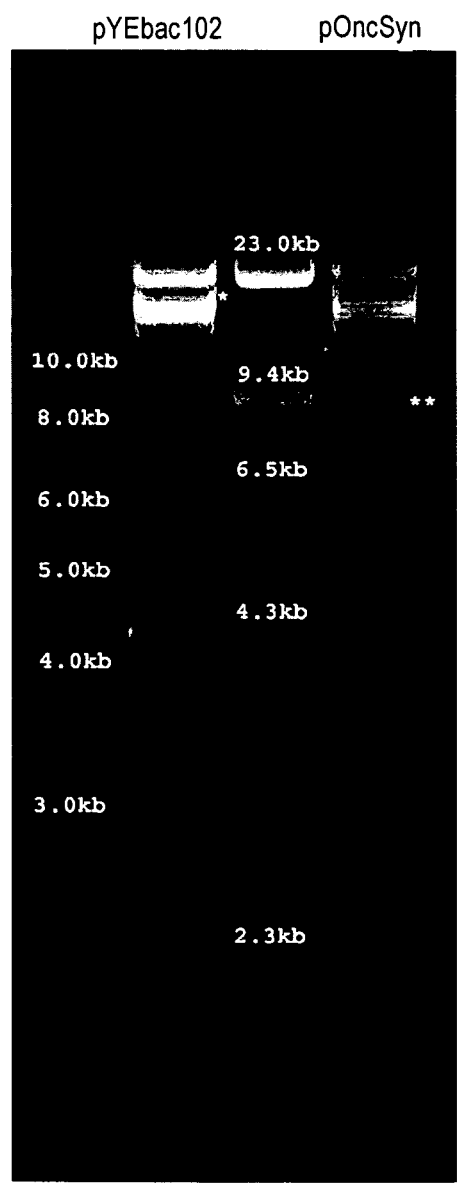
FIG. 2 is a photograph of a restriction fragment analysis of pYEbac102 and pOncSyn, using an ethidium bromide-stained agarose gel in which EcoRI restricted pOncSyn and pYEbac102 DNAs were electrophoretically separated and compared. The deletion of approximately 16 Kbp originating from the E+K EcoRI DNA fragments (apprx. 21.5 Kbp; *) and insertion of approximately 3.2 Kbp sequences containing the RFP gene cassette caused the appearance of a new diagnostic DNA fragment of approximately 8.7 Kbp (**). DNA molecular mass markers are indicated above the respective DNA species.
Figure 3B:
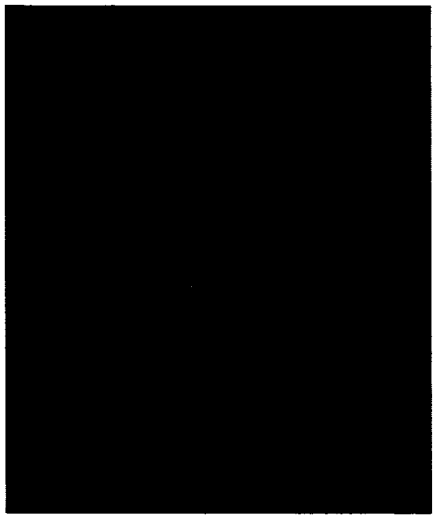
FIG. 3 illustrates the plaque morphology of the Onc and OncSyn viruses. Vero (A, B) and MDA-MB-435S-luc (C, D) cells were infected with either Onc (A, C) or OncSyn (B, D) viruses. Individual viral plaques were photographed at 48 hr post infection using a fluorescence microscope at 100× magnification.
Figure 3D:
Figure 3A:
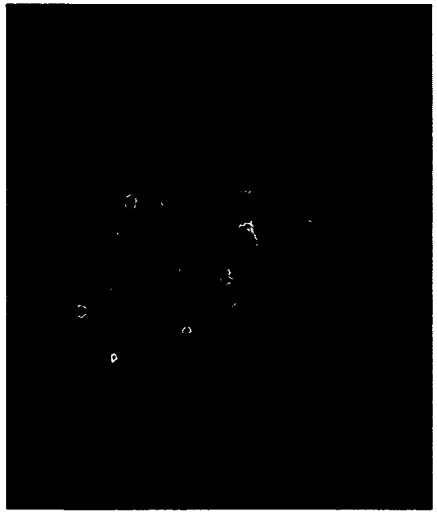
Figure 3C:
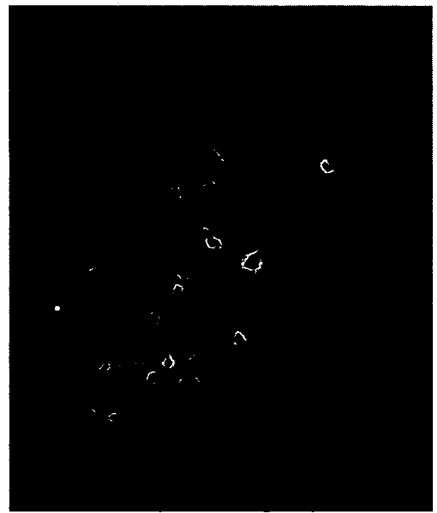

To facilitate further characterization of the OncSyn genome and the rapid construction of additional OncSyn recombinant viruses containing other transgenes of interest, the OncSyn genome was recovered in *E. coli* as a bacterial artificial chromosome (bac), since it contained the original bac plasmid sequences originating from pYEbac102. The recovered pOncSyn and parental pYEbac102 plasmid DNAs were subjected to restriction endonuclease analysis as means for determining overall genomic stability. FIG. 2 is a photograph of a restriction fragment analysis of pYEbac102 and pOncSyn, using an ethidium bromide-stained agarose gel in which EcoRI restricted pOncSyn and pYEbac102 DNAs were electrophoretically separated and compared. The deletion of approximately 16 Kbp originating from the E+K EcoRI DNA fragments (apprx. 21.5 Kbp; *) and insertion of approximately 3.2 Kbp sequences containing the RFP gene cassette caused the appearance of a new diagnostic DNA fragment of approximately 8.7 Kbp (**). DNA molecular mass markers are indicated above the respective DNA species.

EcoRI restriction revealed that the cloned OncSyn genome produced a similar restriction pattern to the parental pYEbac102 with the exception of the appearance of a new diagnostic DNA fragment of approximately 8.7 Kbp produced after deletion of approximately 16 Kbp from the E+K EcoRI DNA fragment (apprx. 21.5 Kbp) and insertion of approximately 3.2 Kbp sequences containing the RFP gene cassette (FIG. 2). A similar restriction pattern was produced by EcoRI restriction of the R7020 viral genome (Meignier et al., 1988).

EXAMPLE 3

OncSyn

Phenotypic and Replication Characteristics of the Onc and OncSyn Viruses

The plaque morphology of the Onc and OncSyn viruses was examined on Vero, as well as on cancer cells of different lineages including the MDA-MB-435S-luc (MM4L) (human breast tumor-derived), Hs578T (human breast tumor-derived) and 4T1 (mouse mammary tumor-derived) (see Example 1 above). Both viruses (Onc and OncSyn) produced plaques emitting strong red fluorescence on all cell lines tested. FIG. 3 illustrates the plaque morphology of the Onc and OncSyn viruses. Vero (A, B) and MDA-MB-435S-luc (C, D) cells were infected with either Onc (A, C) or OncSyn (B, D) viruses. Individual viral plaques were photographed at 48 hr post infection using a fluorescence microscope at 100× magnification.

Importantly, both Onc and OncSyn viral plaques were substantially larger on both MM4L (FIG. 3: C, D) and Hs578T (not shown) cells in comparison to Vero cells (FIG. 3: A, B).

To better visualize the extent of virus-induced cells fusion and syncytial plaque morphology of the OncSyn virus, Vero and MM4L cells were infected with HSV-1 (F), Onc, or OncSyn viruses at either low (0.01) or high (1) MOI, and infected cells were visualized at 48 hr post infection by immunohistochemistry using polyclonal antibody against HSV-1 glycoproteins (FIG. 4). FIG. 4 illustrates the plaque phenotypes of HSV-1(F), Onc, and OncSyn viruses. The plaque phenotypes of HSV-1(F), Onc, and OncSyn viruses were observed on Vero (A to F) and MM4L (G to L) cells. Near confluent cell monolayers were infected with wild-type HSV-1(F) derived from pYEbac102 (A, B, G, and H), Onc (C, D, I, and J), and OncSyn (E, F, K, and L) at low (A, C, E, G, I, and K) and high (B, D, F, H, J, and L) MOI. Viral plaques were visualized at 48 hr post infection by immunohistochemistry.

Onc and OncSyn viral plaques were substantially larger on both MM4L (FIG. 4: I, K) and Hs578T (not shown) cells in comparison to Vero cells (FIG. 4: C, E). In contrast, viral plaques on 4T1 cells (breast cancer cells of mouse origin) were drastically smaller (apprx. 10-fold smaller) than those produced on MM4L cells (data not shown). In contrast to the Onc virus, the OncSyn virus produced syncytial plaques, which were larger in MM4L cells than on Vero cells (FIG. 4: K, E). Extensive cell fusion was produced by infection with OncSyn virus at high MOI characterized by large syncytia formed in the entire cell culture dish (FIG. 4: F, L).

Figure 5:
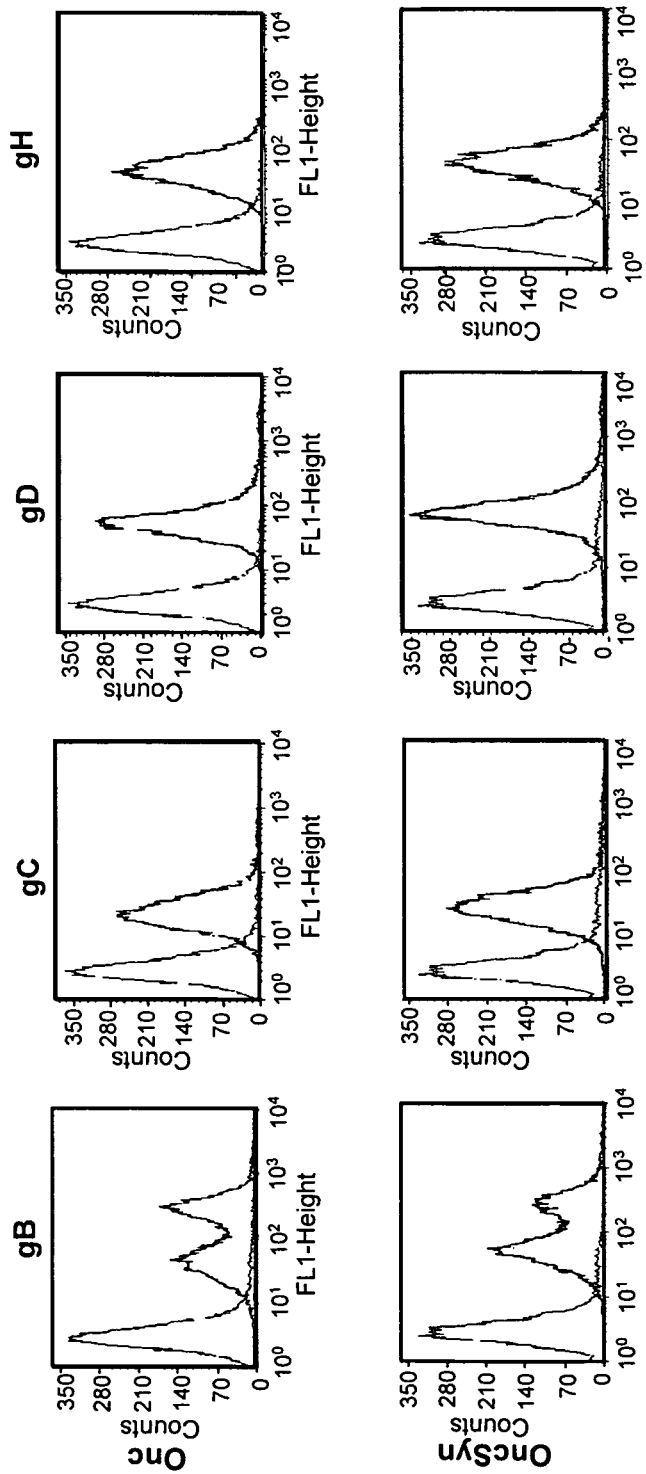
FIG. 5 illustrates the results of a standard fluorescence-activated cell sorter (FACS) analysis of the expression of glycoproteins B, C, D, and H in VERO cells infected with Onc and OncSyn viruses and reacted with anti-gB, anti-gC, anti-gD, and anti-gH antibodies and FITC-conjugated secondary antibodies. The first fluorescence intensity peak represents mock-labeled control cells, while the shifted peaks immediately adjacent to the mock peak represent the antibody-labeled cells.

The immunohistochemistry results revealed that the Onc and OncSyn viruses appeared to express similar amounts of viral glycoproteins detected by the anti-HSV-1 polyclonal serum (FIG. 4). To further assess whether individual viral glycoproteins were expressed on Onc and OncSyn-infected Vero cells, the expression of the major glycoproteins gB, gC, gD and gH was detected by immunofluorescence cytometry. Individual fluorescent cytometric measurements were performed using monoclonal antibodies specific for glycoproteins gB, gC, gD, and gH as described in Example 1. FIG. 5 illustrates the results of the FACS analysis. The first fluorescence intensity peak represents mock-labeled control cells, while the shifted peaks immediately adjacent to the mock peak represent the antibody-labeled cells. These experiments revealed that all viral glycoproteins were detected on infected cell surfaces and that the gBsyn3 mutation did not appear to affect gB expression (FIG. 5).

Figure 6A:
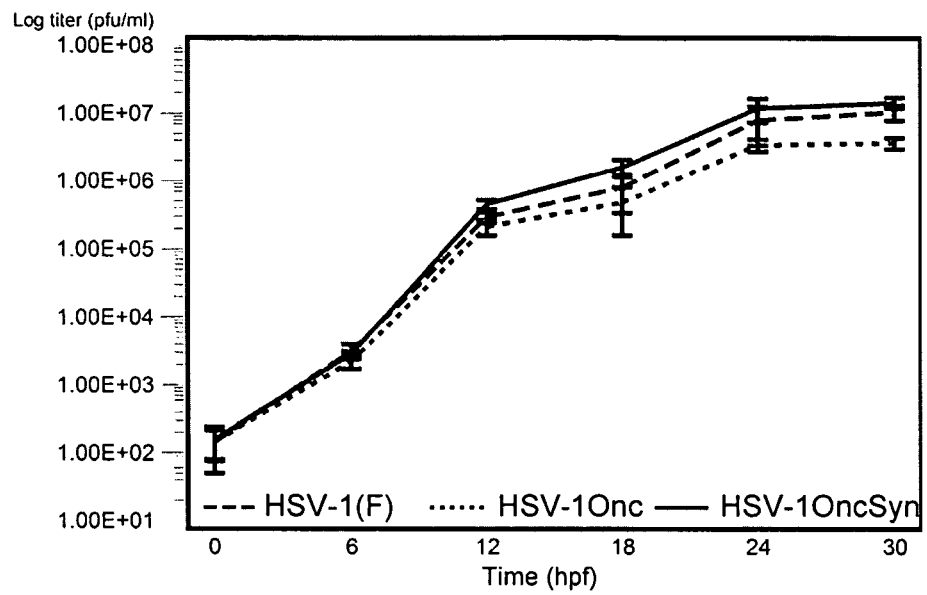
FIG. 6 illustrates the production of infectious virus on Vero and MDA-MB-435S-luc (MM4L) cells, and compares the viral replication kinetics of HSV-1(F), Onc, and OncSyn viruses on Vero (A) and MM4L (B) cells. Onc-step kinetics of infectious virus production were calculated after infection of near confluent monolayers of Vero and MM4L cells at an MOI of 2 followed by incubation at 37° C. Viral titers are shown in logarithmic scale. The error bars represent means±2 standard errors.
Figure 6B:
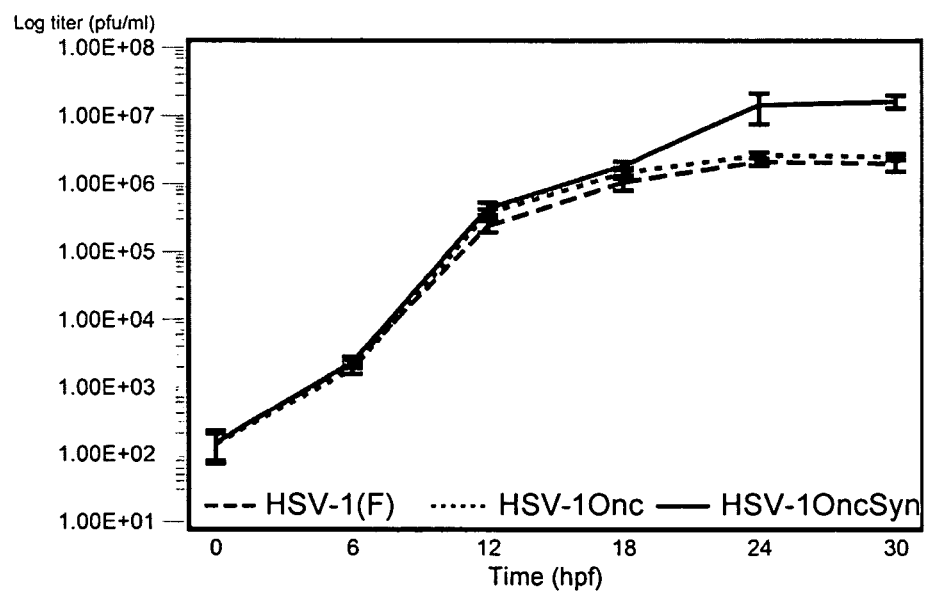

The time-dependent replication characteristics of the HSV-1 (F), Onc and OncSyn viruses were examined in Vero and MM4L cells infected at an MOI of 2. FIG. 6 illustrates the production of infectious virus on Vero and MDA-MB-435S-luc (MM4L) cells, and compares the viral replication kinetics of HSV-1(F), Onc, and OncSyn viruses on Vero (A) and MM4L (B) cells. Onc-step kinetics of infectious virus production were calculated after infection of near confluent monolayers of Vero and MM4L cells at an MOI of 2 followed by incubation at 37° C. Viral titers are shown in logarithmic scale in FIG. 6. The error bars represent means±2 standard errors. The OncSyn virus replicated to higher titers than the parental HSV-1 (F) and Onc viruses in MM4L cells, while OncSyn produced similar titers to the HSV-1(F) virus, but higher titers than Onc in Vero cells (FIG. 6: A, B). Replication of both Onc and OncSyn viruses in 4T1 cells was reduced by more than 2-logs in comparison to MM4L cells (not shown).

EXAMPLE 4

OncSyn

Testing of the Oncolytic Properties of the OncSyn Virus in a Xenograft Nude Mouse Model The human breast cancer cell line MDA-MB-435S (MM4) was isolated from a human ductal carcinoma from a pleural metastatic site and has served as a model for numerous anti-tumor studies (Caillou, 1978). The MM4L cell line constitutively expresses the luciferase gene from the firefly (*Photinus pyralis*). This cell line was previously shown to facilitate visualization of tumor formation and metastasis in a xenograft mouse model (e.g., Leuschner et al., 2003). In this mouse model, MM4L cells are injected into the interscapular region of mice with Matrigel, which promotes efficient tumor establishment (Bao et al., 1994). Vascularization of the primary tumor is typically observed within 10 days after tumor cell inoculation.

Subcutaneous tumors were established in female athymic Hsd-nu nude mice. When the average volume of tumors reached 70-80 mm$^3$, mice were randomly assigned to groups (n=24) and were treated with intratumor injections of OncSyn virus, PBS, or heat and UV inactivated OncSyn virus at multiple sites of the tumors on days 22, 25, and 28 after tumor cell inoculation. Half of the mice (n=12) in each group were humanely sacrificed 5 days after the last injection. The remaining animals in each group (n=12) received a second round of 3 consecutive injections at days 34, 37, and 40. These animals were humanely sacrificed 5 days after the last injection.

Figure 7:
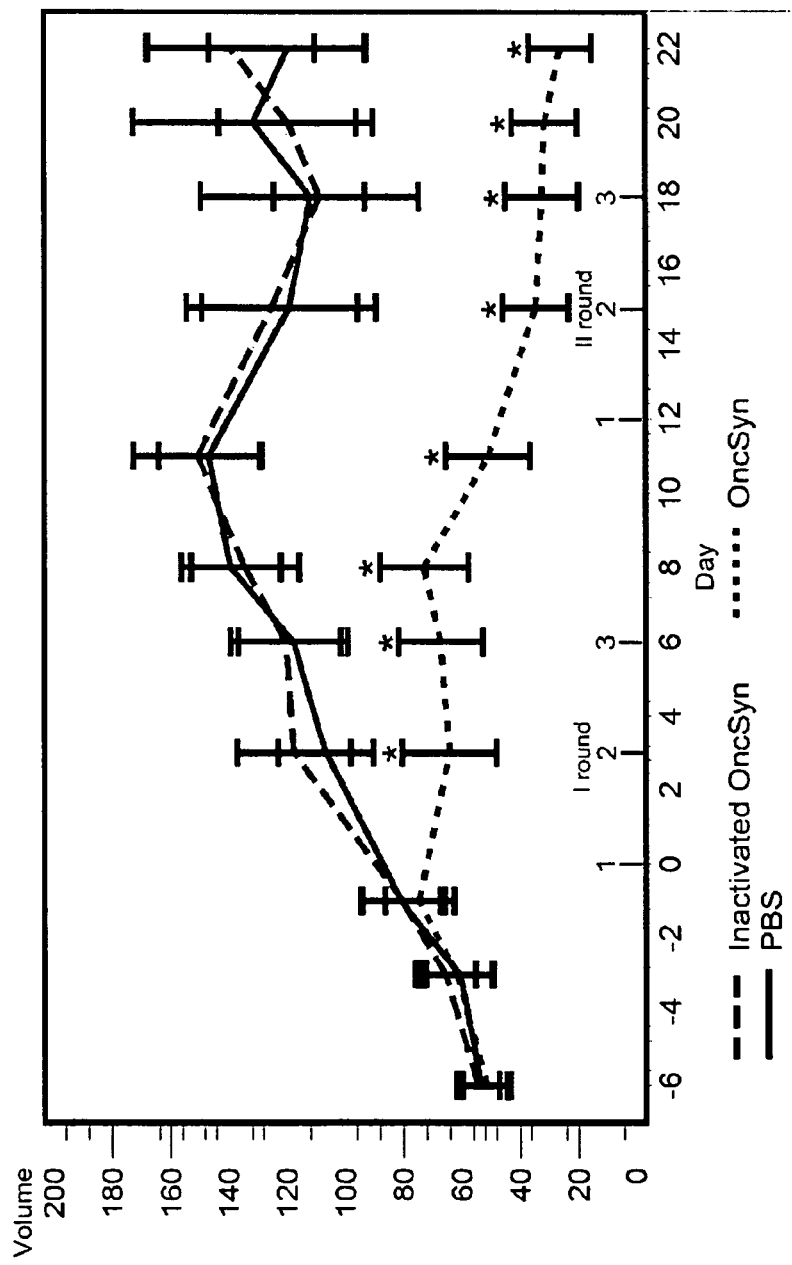
FIG. 7 illustrated the effect of inactivated and active OncSyn on tumor volumes established by injecting MM4L cells as a Matrigel suspension subcutaneously into the interscapular regions of mice. Tumor volumes were measured prior to (negative values) and after the injections. The "0" on X axis represents the day of the first injection. The vertical lines on X axis represent the injection days for 1 and II rounds of injections (3 consecutive injections per round). The error bars represent means±2 standard errors. Within a given day of measurement, significant differences (p<0.05) are indicated with an asterisk (*).
Figure 8A:
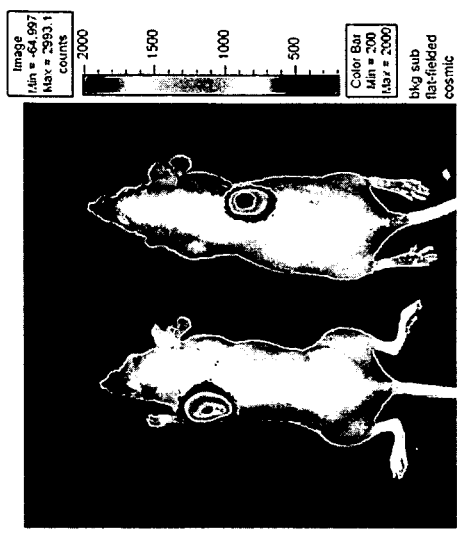
FIG. 8 illustrates the results of chemiluminescence imaging of MM4L tumors in living female nude mice, treated either with inactivated OncSyn (A), PBS (B) or OncSyn (C, D). Pictures shown represent animals after the first round of injections consisting of 3 intratumor injections of the OncSyn viral particles, PBS, or heat and UV inactivated OncSyn. Color bars show the scale of minimum and maximum light intensities depicted on the Fig.
Figure 8B:
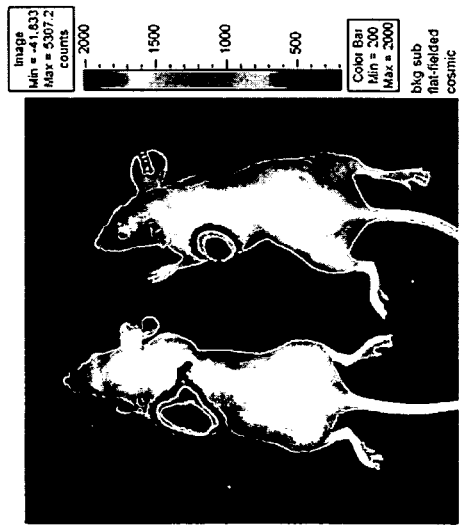
Figure 8C:
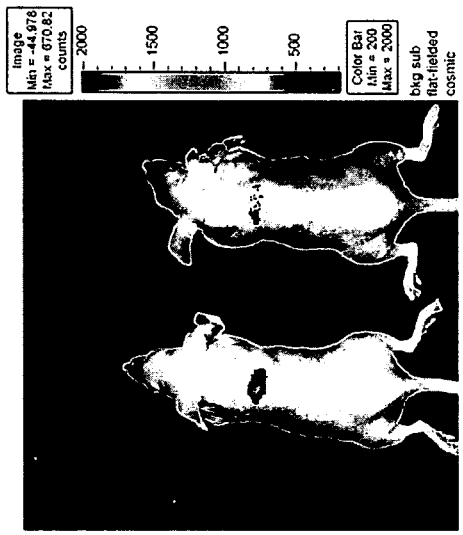
Figure 8D:
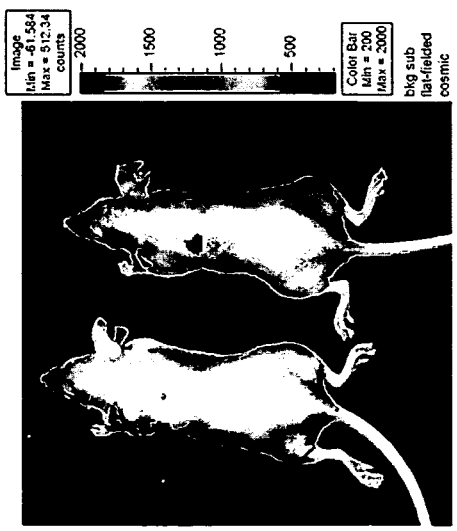

FIG. 7 illustrates the effect of treatment with active and inactivated OncSyn on tumor volumes. Human breast tumor xenografts were established by injecting MM4L cells as a Matrigel suspension subcutaneously into the interscapular regions of mice. Tumors were measured using a digital caliper at defined time intervals prior and after treatment (x-axis). Groups of mice were treated with OncSyn, inactivated Syn, or PBS. OncSyn, inactivated OncSyn, or PBS was injected intratumorally when tumors reached approximately 70-80 mm$^3$ volume. Tumor volumes were measured prior to (negative values) and after the injections. The "0" on X axis represents the day of the first injection. The vertical lines on X axis represent the injection days for I and II rounds of injections (3 consecutive injections per round). The tumor volumes were determined from the formula: volume=(length×width×height)/2. The error bars represent means±2 standard errors. Within a given day of measurement, significant differences (p M 0.05) are indicated with an asterisk (*).

Tumors inoculated with a double round of OncSyn virus exhibited a time-dependent decrease in tumor size with maximum reduction of more than 80% of controls when observed at 22 days post first injection with the virus (FIG. 7). Prior to the virus injections, tumor sizes of the test group were similar to those of the two control mouse groups injected with either PBS (p=0.90) or inactivated OncSyn virus (p=0.84). Tumors of mice injected only with one round of virus injections exhibited a rapid reduction of tumor size at three days after the first injection (FIG. 7). When compared statistically at each period to both the inactivated OncSyn group and the PBS group, the OncSyn group showed highly significant (p<0.0001) reductions in tumor size from this period until the end of the study. The efficacy of treatment was not influenced by differential weight gain/loss in different mouse groups, since analysis of mouse weights during the course of the study showed no significant differences among the three groups over time. Furthermore, this analysis was corroborated by correlation analysis which indicated consistent weight gain patterns across all three study groups (not shown).

To further substantiate the oncolytic effect of the OncSyn virus on breast tumors implanted in nude mice, tumor progression and cellular viability was evaluated by chemiluminscence imaging. A total of eight mice per group either after the first or second round of viral treatment were evaluated for the presence of chemiluminescent MM4L cells. FIG. 8 illustrates the chemiluminescence imaging of MM4L tumors in living female nude mice. Each image was produced after a 5-7 min exposure starting at 20 min following intraperitoneal injection of D-Luciferin (150 mg/kg of body weight). The images of 8 animals are shown. The signal intensity in the region of interest (ROI) is expressed as light counts. Tumors were treated either with inactivated OncSyn (A), PBS (B) or OncSyn (C, D). Pictures shown represent animals after the first round of injections consisting of 3 intratumor injections of the OncSyn viral particles, PBS, or heat and UV inactivated OncSyn. Injections per tumor contained 2×10$^6$ viruses per injection in a 250-μl volume, 250 μl of PBS, or 250 μl of heat and UV inactivated OncSyn. Color bars show the scale of minimum and maximum light intensities depicted on the FIG. 8.

OncSyn-treated mice (FIG. 8: C, D) exhibited drastic reduction in chemiluminescence signals emitted from tumor injection sites in comparison with the PBS and inactivated virus control injections (FIG. 8: A, B, respectively). Similar results were obtained for OncSyn-treated mice receiving two rounds of injections (not shown).

Figure 9:
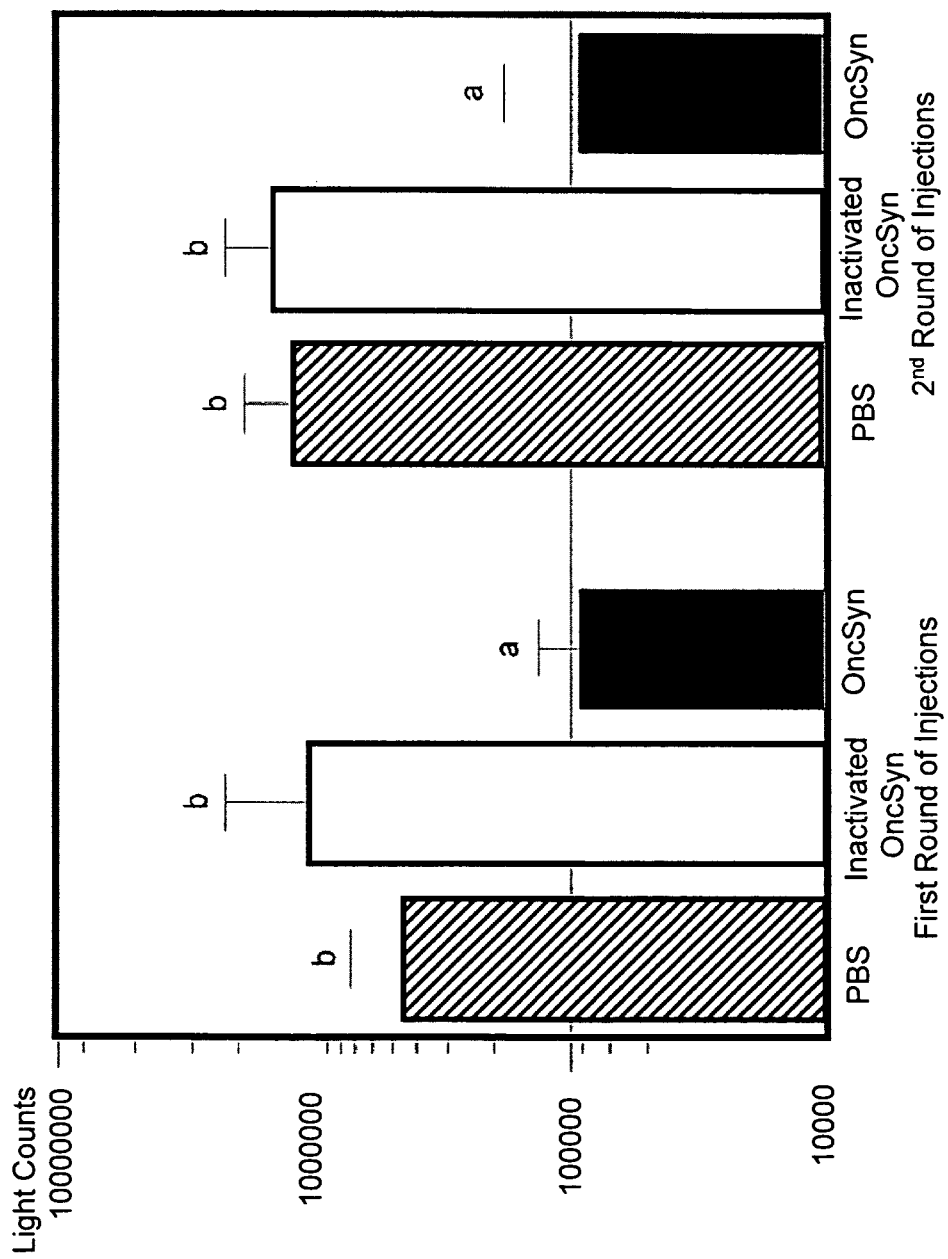
FIG. 9 is a graphic representation of the relative light intensities of chemiluminescent mouse tumors, after the first and second rounds of injections with PBS, inactivated virus, or OncSyn virus. Light counts are set in logarithmic scale, and the error bars represent 95% confidence limits. Means with the same letter in common are not significantly different (p>0.05) within each round of injections.

The chemiluminscence signals were quantified using relative light counts detected by the equipment. FIG. 9 is a graphic representation of the relative light intensities of chemiluminescent mouse tumors, after the first and second rounds of injections with PBS, inactivated virus, or OncSyn virus. Light intensity was measured in a chemiluminscence whole animal in vivo imaging system (IVIS 50). Light counts are set in logarithmic scale. The error bars represent 95% confidence limits. Means with the same letter in common are not significantly different (p>0.05) within each round of injections. Comparison of these measurements revealed a decrease of up to 90% of light counts for the Onc Syn virus-treated animal tumors compared to the control PBS or inactivated virus treated groups for both the single (p=0.0002) or double (p<0.0001) rounds of injections (FIG. 9).

EXAMPLE 5

OncSyn

Pathological Examination of Tumors and Internal Organs

Figure 10A:
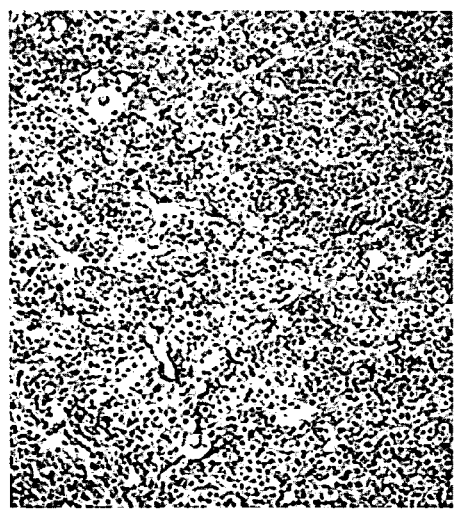
FIG. 10 illustrates the histopathology of MM4L tumors, treated by three consecutive injections (one round). The infected and treated mice were sacrificed 5 days after the last injection. Representative stained sections (stained with H and E) are shown for inactivated OncSyn (FIG. 10A), PBS (FIG. 10B), and OncSyn (FIG. 10C). Also visible are necrotic tumor cells (N) within the matrigel matrix (homogenous pale eosinophilic material). All photographs were taken at 200× magnification.
Figure 10B:
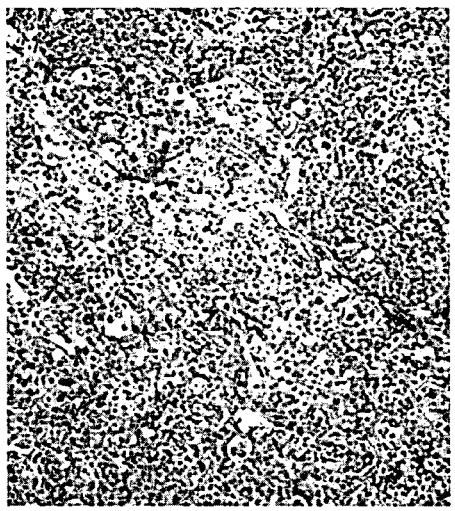
Figure 10C:
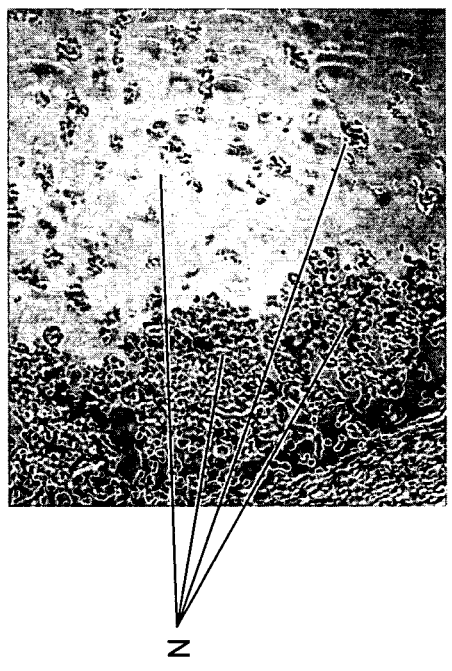

Individual tumors were removed, fixed for histopathological examination, and evaluated by blind observation with regard to the level of observed necrosis, presence of inflammatory cells, and any other abnormal morphological effects. Typically, most tumors had a connective tissue capsule formed around the tumor. In addition, vascular invasion into the tumor occurred from the connective tissue capsule. FIG. 10 illustrates the histopathology of MM4L tumors, treated by three consecutive injections (one round), 5 days after the last injection. Tumor-derived tissues were stained with H and E and examined. Representative stained sections are shown for inactivated OncSyn (A), PBS (B), and OncSyn (C). In FIGS. 10A and 10B, viable tumor cells are seen throughout the histosection. In contrast, in FIG. 10C, viable tumor cells are greatly reduced in number and are admixed with necrotic tumor cells (N). Also visible are necrotic tumor cells (N) within the matrigel matrix (homogenous pale eosinophilic material). All photographs were taken at 200× magnification. Thus, OncSyn-treated tumors had a high level of necrotic MM4L cells (FIG. 10).

Figure 11:
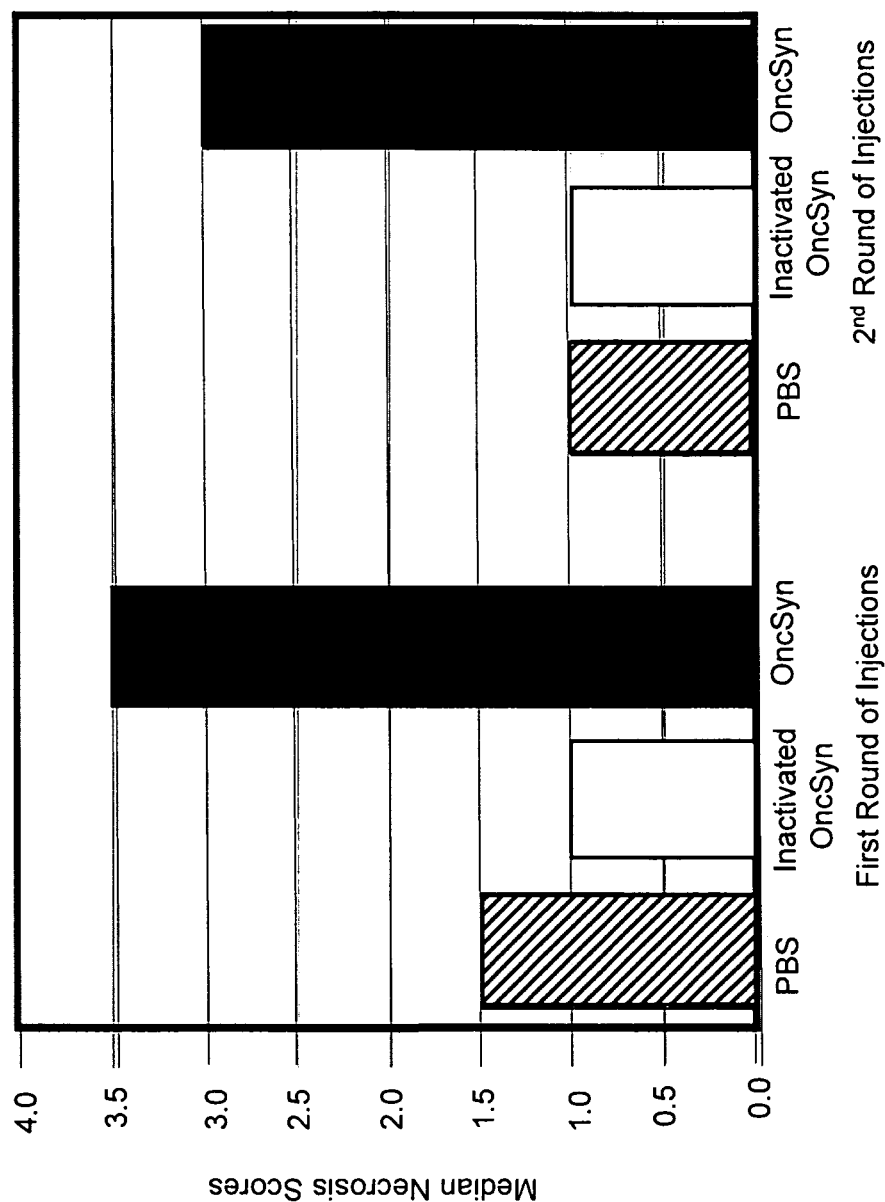
FIG. 11 shows the median tumor necrosis scores (graded on a 0 to 4 scale) determined by histopathological examination, as determined for tissue samples obtained after one and two rounds of treatment with inactivated OncSyn virus, PBS, or OncSyn virus.

The approximate amount of tumor cell necrosis was determined for each tumor histo-section. A grading scale of 1-4 was used with 4 being the highest. FIG. 11 shows the median tumor necrosis scores determined by histopathological examination, as determined for tissue samples obtained after one and two rounds of treatment with inactivated OncSyn virus, PBS, or OncSyn virus. The OncSyn virus caused a significant increase in necrotic tumor cells after either the single (p<0.0001) or double (p=0.0002) treatment with the OncSyn virus (FIG. 11). After the single treatment, there were also highly significant negative correlations between scores and tumor weights (r=−0.80, p<0.0001) and tumor volumes (r=−0.68, p<0.0001). (Data not shown) After the double treatment these values were again significant with r=−0.63 (p<0.0001) and r=−0.57 (p=0.0004), respectively. (Data not shown) Microscopic examination of all lung lobes, liver, spleen, and kidneys of all the animals did not reveal any abnormalities.

The above experimental results indicate the following: 1) the OncSyn virus replicated to high titers in Vero and especially in human breast cancer cells and caused extensive virus-induced cell fusion; 2) the OncSyn virus drastically reduced tumor sizes after a single round of direct intratumor injections of human breast tumors established in nude mice; 3) the OncSyn genome was recovered as a stable bacterial artificial chromosome to enable future rapid modifications; and 4) pathological evaluation of tumor tissues revealed extensive necrosis after a single round of virus injections. These results indicate that the OncSyn virus could effectively treat breast and other types of tumors and form the basis for generation of additional recombinant viruses that could be effectively used for human cancer treatment.

The OncSyn virus has some similarities, as well as substantial differences in comparison to NV1020. Both OncSyn and R7020 viruses are derived from the HSV-1(F) strain, with the exception that OncSyn virus was derived from the HSV-1(F) genome cloned into a bacterial artificial chromosome (pYEbac102) (Tanaka et al., 2003). It has been reported that the pYEbac102-derived virus exhibited similar virulence profile to the parental HSV-1(F) strain in intracerebral infections (Tanaka et al., 2003). However, immunocompetent Balb/c mice infected with the pYEbac102-derived virus via the intraperitoneal route (i.p.) did not exhibit any neurological symptoms suggesting that the pYEbac102-derived virus may be attenuated (not shown). Extensive restriction analysis and DNA sequencing of the pYEbac102-derived virus did not reveal any significant genomic changes, suggesting that either the insertion of the bac (bacterial artificial chromosome) backbone or other nucleotide changes may potentially contribute to the observed attenuation characteristics (unpublished observations). Both NV1020 and OncSyn contain a large deletion of approximately 16 kilobase-pairs (Kbp) across the joint region of the long-L and short-S components of the viral genome. This deleted region includes the UL56 gene, and one of the two copies of $\alpha 0$, $\gamma_1$ 34.5 and $\alpha 4$ genes. In addition, this deletion also includes the entire genomic region coding for one of the two loci encoding the latency-associated transcripts (LAT). The NV1020 virus contains within the deleted genomic region a 5.2 Kbp DNA fragment of HSV-2 and an exogenous copy of the HSV-1 viral thymidine kinase (TK) under the control of the $\alpha 4$ promoter (the native TK gene has been deleted). In contrast, the OncSyn virus contains within the deleted genomic region an insertion of a gene cassette coding for the red fluorescence protein under the constitutive control of the EF-1$\alpha$ promoter, while the native TK gene remains unaltered. The presence of both HSV-1 and HSV-2 glycoproteins gD, gI and gE in the NV1020 virus may lower the relative efficiencies of intracellular virus assembly and egress, and result in virus attenuation and decreased intra-tumor spread (Hu and Coffin, 2003). Alternatively, it is possible that the presence of the HSV-2 viral glycoproteins, especially gD and gE/gI may broaden the host-range of the recombinant virus. The NV1020 virus has been recently shown to be safe in human trials in a recent Phase I, open-label, dose-escalating study for subjects with metastatic colorectal carcinoma to the liver (Kemeny et al., 2006), as well as efficacious in combination with chemotherapy (Gutermann et al., 2006). One of the potential significant advantages of the NV1020 over the G207 virus is that it may require lower viral doses to achieve therapeutic effects. Furthermore, it is believed that the OncSyn virus may be delivered in lower viral doses than the NV1020 virus due to its potential advantage in virus production and intratumor spread over the NV1020 virus.

The OncSyn virus was constructed to specify the gBsyn3 mutation, which is known to cause extensive virus-induced cell fusion (Bzik et al., 1984a; Pellett et al., 1985). Infection of a variety of breast cancer cells, as well as other cell lines such as Vero, HeLa, etc., revealed that OncSyn caused extensive virus-induced cell fusion. Apparently, the syncytial phenotype provided a significant replication advantage for the virus, since the OncSyn titers were higher than those of the parental Onc virus in all cells tested. Surprisingly, the OncSyn virus produced higher viral titers than the HSV-1(F) prototypic virus in MM4L cells indicating that the increased virus spread caused by the gBsyn3 mutation substantially overcame the reduced plaque phenotype caused by the NV1020 genomic deletion. In addition to the $\gamma_1$ 34.5 important anti-interferon functions, the $\gamma_1$ 34.5 protein is known to function in virus maturation and egress from infected cells, as well as glycoprotein synthesis and cell-surface expression (Brown et al., 1994; Mao and Rosenthal, 2003; Jing et al., 2004; Jing and He, 2005). Therefore, the gBsyn3 mutation may reverse these defects by allowing more efficient virus intracellular transport and egress.

EXAMPLE 6

OncdSyn

Materials and Methods

Cells: African green monkey kidney (Vero) cells and mouse mammary tumor cells (4T1) (Aslakson and Miller, 1992) were obtained from the American Type Culture Collection (Manassas, Va.). Vero cells were maintained in Dulbecco's modified Eagle's medium (Gibco-BRL; Grand Island, N.Y.), supplemented with 10% fetal calf serum (FCS) and antibiotics. 4T1 cells were maintained in RPMI 1640 medium (Hyclone, Logan, Utah) containing 10% FCS. The cultures were maintained at 37° C. in a humidified atmosphere of 5% $CO_2$/95% air.

Construction of the doubly fusogenic recombinant virus HSV-1 OncdSyn. The previously discussed OncSyn viral genome was recovered as a bacterial artificial chromosome (bac) into *E. coli* (pOncSyn). (See above) This artificial chromosome was used for the construction of pOncdSyn bac plasmid utilizing a new methodology—the double-red mutagenesis technique in *E. coli* (Tischer et al., 2006) enabling the markerless introduction of the gKsyn1 mutation (Ala-to-Val at aa 40). The OncdSyn virus was recovered after transfection of Vero cells with the pOncdSyn plasmid. The OncdSyn viral genome and the pOncdSyn bac were extensively characterized by diagnostic PCR and DNA sequencing to ensure the stability of the viral genomes, the presence of the parental Onc deletions and the presence of the gKsyn1 mutation within the gK gene, as described above for the OncSyn virus.

Phenotypic characterization and replication kinetics of the OncSyn and OncdSyn viruses. Cells (both Vero and 4T1) were seeded into 6-well plates and infected the following day (when they reached approximately 95% confluency) with the OncSyn or OncdSyn viruses at a multiplicity of infection (MOI) ranging from 0.001-1 plaque forming units per cell (PFU/cell). Cells were cultured in a maintenance medium (containing 2% FCS) and were left for 2 days to allow for the plaques and the cell fusion to develop. Photographs of the infected cells were taken using a fluorescence microscope. For assessment of viral plaque morphologies, Vero and 4T1 cells were infected with HSV-1(F), OncSyn or OncdSyn viruses, and visualized after immunohistochemistry at 48 hours post-infection (h.p.i.) using horseradish peroxidase-conjugated anti-HSV antibody (Dako, Carpinteri, Calif.) and Novared substrate development kit (VectorLabs, Burlingame, Calif.).

To determine the replication kinetics of the viruses, one-step growth kinetics were performed as described previously (Foster, Alvarez, and Kousoulas, 2003; Foster, Rybachuk, and Kousoulas, 2001). Briefly, nearly confluent monolayers of either Vero or 4T1 cells were infected with each virus at an MOI of 2 at 4° C. for 1 h. Thereafter, virus was allowed to penetrate for 2 h at 37° C. Any remaining extracellular virus was inactivated by low-pH treatment with phosphate buffered saline at pH 3.0. Cells and supernatants were harvested immediately thereafter (0 h) or after 12 or 24 h of incubation at 37° C. Virus titers were determined by endpoint titration of virus stocks on Vero cells.

Animal experiments: Female Balb/c mice were obtained from Harlan (Indianapolis, Ind.) and housed in an animal room which was kept at 25° C. with a 12 hour light-dark cycle. All experimental procedures involving animals were approved by the local institutional animal care and use committee (IACUC). At 6-7 weeks of age the animals (19-20 g body weight) were implanted subcutaneously in the interscapular area with $1 \times 10^5$ viable 4T1 cells suspended in 0.2 ml of PBS using a 27 gauge needle. Body weights were determined weekly, and tumor sizes were monitored beginning 7 days after tumor inoculation by direct measuring with a digital microcaliper. Tumor volumes were calculated using the following formula: volume=(length×width×height)/2. At an average tumor volume of approximately 80-90 mm³ (first experiment) or 35-40 mm³ (second experiment), animals were randomized into 3 groups (first experiment) or 2 groups (second experiment) using a randomization plan developed by Dr. Gerard E. Dallal and available online (Randomization.com). The groups of mice received 3 intratumoral injections of the OncSyn or OncdSyn viral particles, or PBS every four days for the first experiment and injections of the OncdSyn or PBS every third day for the second experiment. Each tumor was injected with approximately $1 \times 10^6$ viruses per injection in 250 µl volume, while control mice received 250 µl PBS. Injections were performed slowly at 3 different sites per tumor. On day 42 for the first experiment and day 33 for the second experiment after initial tumor cell implantation, mice were humanely euthanized in a $CO_2$ chamber and subjected to gross as well as microscopic histological examination. Lung and other internal organ metastases were counted using a dissecting microscope after placing the resected organs in fixative for 24 hours. The primary tumor site, lungs, heart, liver, spleen, and kidneys from each animal were fixed in 10% neutral buffered formalin, trimmed, paraffin embedded, sectioned, stained with hematoxylin and eosin (H&E), and evaluated by light microscopy.

Statistical methods and analyses. The SAS® statistical package (Version 9.1.3) was used for the analyses of the in vivo studies. Distributions were examined for normality using the UNIVARIATE procedure with a Shapiro-Wilk test of normality. For the repeated measures part of the analyses of tumor volumes and tumor weights, the GLM procedure was used to conduct a repeated measures design analyzed as a split-plot arrangement of treatments with TREATMENT (OncSyn, OncdSyn, and PBS) and MOUSE within TREATMENT as main plot factors. Subplot factors included PERIOD (days of measurements) and TREATMENT by PERIOD interaction. When overall analyses determined significance ($p \leq 0.05$), Tukey's HSD test was used to examine pairwise differences for main effects, and pairwise comparisons of least square means with regard to interaction effects were examined with preplanned t-tests. The Wilcoxon Two-Sample test was used to analyze the difference of lung metastatic node counts between PBS and OncdSyn groups.

EXAMPLE 7

OncdSyn

Construction and Characterization of the Oncolytic HSV-1 Mutant Virus OncdSyn

To further increase the ability of the OncSyn virus to cause virus-induced cell fusion, the syncytial mutation gKsyn1

(Ala-to-Val at position 40) known to cause virus-induced cell fusion (Manservigi, Spear, and Buchan, 1977) was introduced into the OncSyn viral genome cloned into a bacterial artificial chromosome (bac) using the markerless double-red mutagenesis method (Tischer et al., 2006). The resultant OncdSyn virus carried syncytial mutations in both gB (syn3) and gK (syn1) (FIG. 12).

FIG. 12 is a schematic representation of the genomic structures of the oncolytic recombinant viruses OncSyn and OncdSyn. The top panel, Panel A, represents the prototypic arrangement of the HSV-1 genome with the unique long (UL) and unique short (US) regions flanked by the terminal repeat (TR) and internal repeat (IR) regions. Panel B indicates the approximate locations of the gB and gK genes. Panel C is an expansion of the inverted repeat region showing the approximate locations of UL54, UL55, UL56, α0, $\gamma_1$34.5, α4, α22 and US2 genes. Panel D is a schematic of the DNA fragment cloned into plasmid pJM-R, which was used for insertion of the HcRed gene cassette into the viral genome in place of the NV1020 genomic deletion as described above in Example 6.

As reported above for the OncSyn virus, the bac-cloned OncdSyn viral genome was subjected to PCR-diagnostic analysis and direct sequencing of specific genomic loci to confirm the presence of the syn3 and syn1 mutations and the previously engineered deletion/insertion at the $\gamma_1$34.5 locus (data not shown).

EXAMPLE 8

Figure 13G:
FIG. 13 shows the plaque morphology of the wild-type HSV-1 (F) (A,D), OncSyn (B,E) and OncdSyn (C, F, G, H) viruses, when infecting nearly confluent Vero (A-C) and 4T1 (D-F) cell monolayers as visualized 48 hr post infection by immunohistochemistry and photographed with a phase contrast or fluorescent microscope.
Figure 13H:
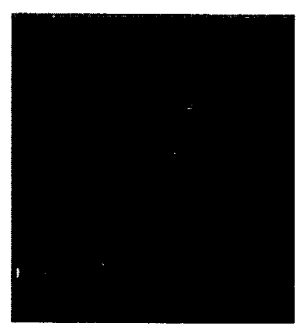
Figure 13C:
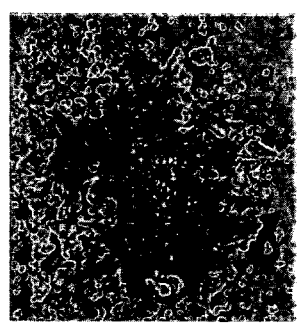
Figure 13F:
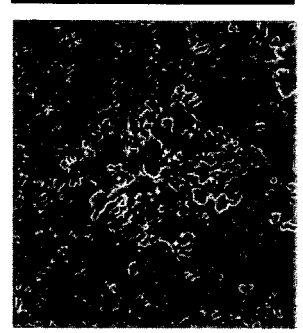
Figure 13B:
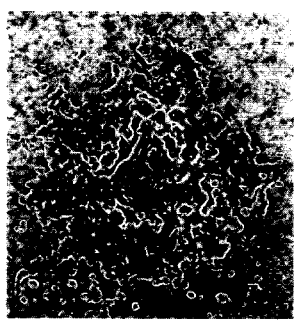
Figure 13E:
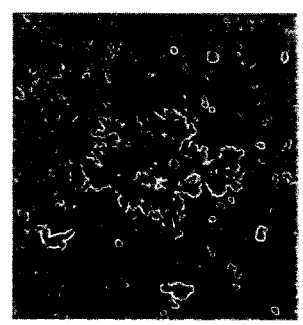
Figure 13A:
Figure 13D:
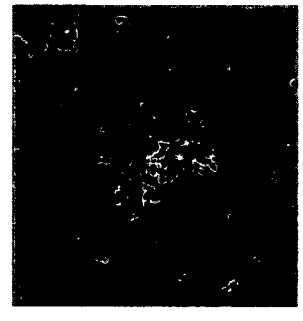

Phenotypic Characteristics of the OncSyn and OncdSyn Viruses on Vero and 4T1 Cells The plaque morphology of the HSV-1(F) OncSyn and OncdSyn viruses was examined on Vero cells and 4T1 cancer cells (Balb/c spontaneous mammary adenocarcinoma-derived) (Aslakson and Miller, 1992) as described above in Example 6. FIG. 13 shows the plaque morphology of the HSV-1 (F), OncSyn and OncdSyn viruses. Nearly confluent Vero (A-C) and 4T1 (D-F) cell monolayers were infected with wild-type HSV-1(F) (A, D), OncSyn (B, E) and OncdSyn (C, F) viruses. Plaque morphologies were visualized on Vero and 4T1 cells at 48 hours post infection (hpi) by immunohistochemistry using a polyclonal anti-HSV-1 antibody (FIGS. 13A-F), and photographed either with a phase contrast or a fluorescent microscope. Viral plaques generated by all three viruses tested were substantially smaller on 4T1 mouse cancer cells (FIGS. 13D-F) in comparison to Vero cells (FIGS. 13A-C). Specifically, the HSV-1(F) wild-type virus, which does not cause extensive virus-induced cell fusion, produced viral plaques on 4T1 cells that were approximately 10-fold smaller than those produced on Vero cells (FIGS. 13D and A). In contrast, the OncSyn and OncdSyn viruses produced syncytial plaques on both cell lines tested (FIGS. 13B, C, E, F). However, both the OncSyn and OncdSyn viral plaques on 4T1 cells were larger than those produced by the HSV-1(F) wild-type virus (FIGS. 13E and F compared to D). The OncdSyn virus appeared to cause more pronounced virus-induced cell fusion on both Vero and 4T1 cells (FIGS. 13C and F). In addition, the OncdSyn viral plaques emitted strong red fluorescence due to constitutive expression of the red fluorescence protein (RFP) expressed under the elongation factor 1α (EF-1α) promoter control (FIGS. 13G and H).

EXAMPLE 9

Kinetics of Viral Replication on Vero and 4T1 Cells

Figure 14A:
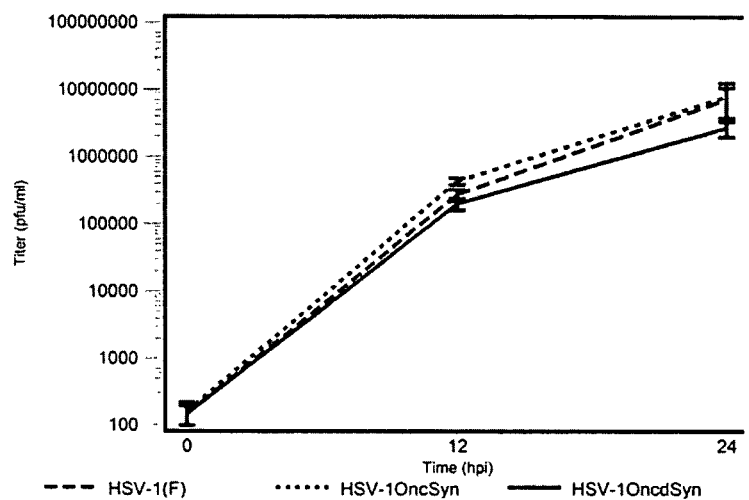
FIG. 14 shows the comparative kinetics of viral replication of wild-type HSV-1(F) and mutant viruses OncSyn and OncdSyn grown on Vero (FIG. 14A) and 4T1 (FIG. 14B), infected at an MOI of 2 with each virus, incubated at 37° C., and the numbers of infectious virions determined at different times post infection. Viral titers (mean plaque forming units (pfu) at each time point) are shown in logarithmic scale, and the error bars represent means±2 standard errors.
Figure 14B:
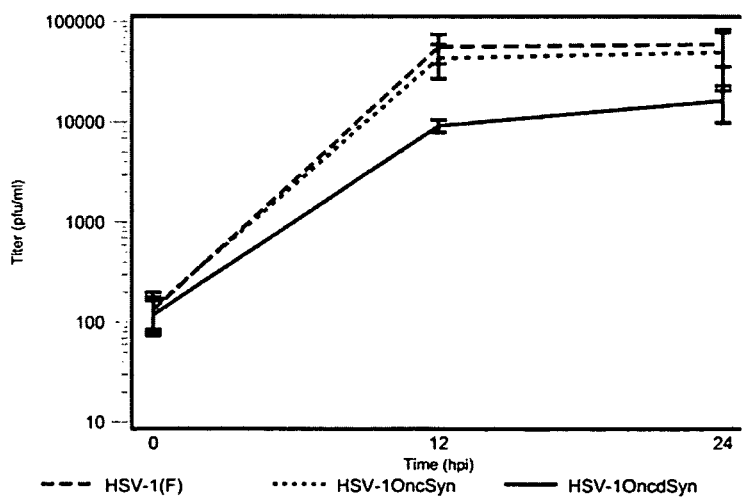

HSV-1(F) and OncSyn viruses replicated to similar titers in Vero cells, while the OncdSyn virus consistently replicated to titers that were a half-log lower than either HSV-1(F), or OncSyn viruses. FIG. 14 shows the comparative kinetics of viral replication of wild-type HSV-1(F) and mutant viruses OncSyn and OncdSyn grown on Vero and 4T1 cells. Near confluent monolayers of Vero (FIG. 14A) and 4T1 (FIG. 14B) cells were infected at an MOI of 2 with each virus and incubated at 37° C., and the numbers of infectious virions were determined at different times post infection. Viral titers (mean pfu at each time point) are shown in logarithmic scale. The error bars represent means±2 standard errors. The kinetics of viral replication were substantially slower in 4T1 cells than in Vero cells, and final titers in 4T1 cells were more than two logs lower for HSV-1(F) and OncSyn, while OncdSyn viral titers were more than three logs lower on 4T1 cells than in Vero cells. In addition, OncdSyn viral titers were approximately one log lower than the HSV-1(F) and OncSyn viral titers on 4T1 cells.

EXAMPLE 10

OncSyn and OncdSyn

Intra-Tumor Virotherapy

Figure 15A:
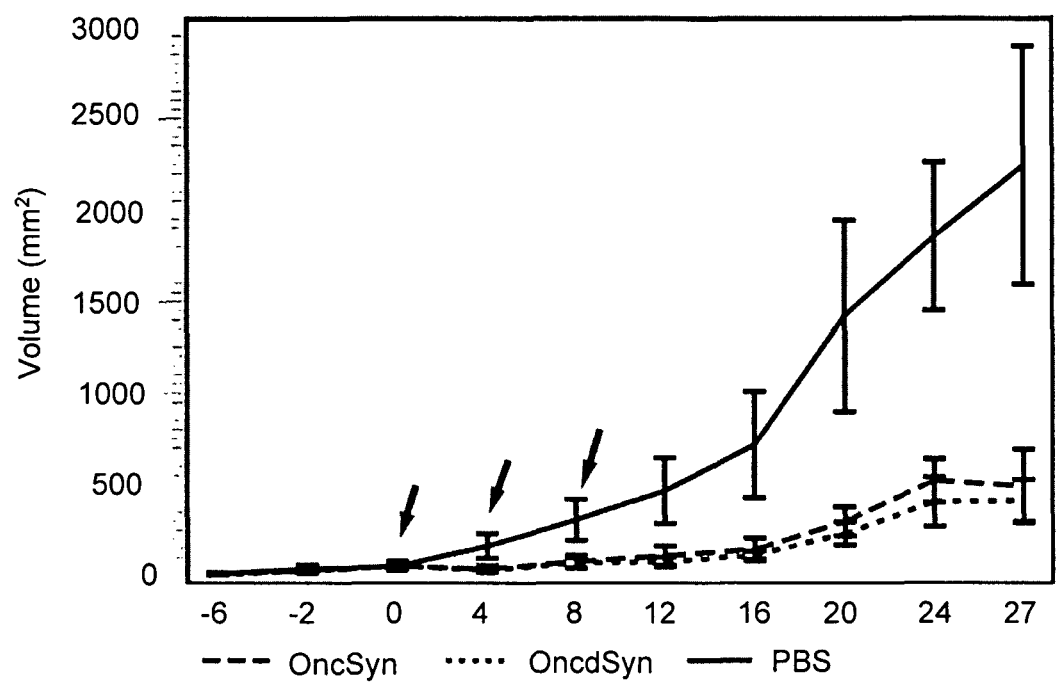
In FIG. 15A, Balb/c mice were implanted subcutaneously in the interscapular area with 1×10$^5$ viable 4T1 cells, and tumors were measured using a digital caliper at defined time intervals prior and after treatment (x axis). Tumors were injected with OncSyn, OncdSyn viruses, or PBS when tumors reached approximately 80-90 mm$^3$ in volume. Arrows indicate the days when therapy was administered. Tumor volumes were measured prior to (negative values on the x axis) and after the injections. "0" on X axis represents the day of the first injection. The tumor volumes were determined from the formula: volume=(length×width× height)/2. The error bars represent means±2 standard errors.
Figure 15B:
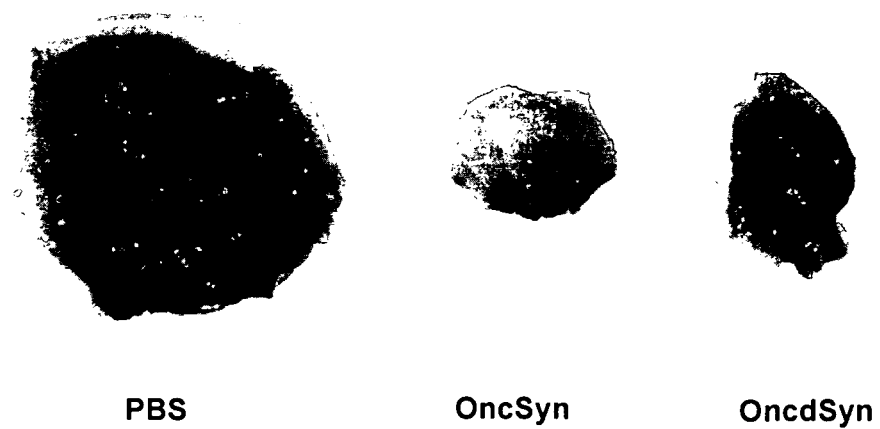
FIG. 15B illustrates representative tumors from virus and PBS treated animals that were excised at 42 days post implantation and visually examined.

4T1 cells were injected subcutaneously in the interscapular regions of Balb/c female mice. When the palpable tumors reached the volume of approximately 80-90 mm$^3$, mice were injected with three consecutive intra-tumor injections of OncSyn and OncdSyn viruses or PBS (control) every four days as described above in Example 6. FIG. 15 illustrates the intratumor treatment with OncSyn and OncdSyn viruses. In FIG. 15(A), Balb/c mice were implanted subcutaneously in the interscapular area with 1×10$^5$ viable 4T1 cells. Tumors were measured using a digital caliper at defined time intervals prior and after treatment (x axis). Tumors were injected with OncSyn virus, OncdSyn virus, or PBS when tumors reached approximately 80-90 mm$^3$ in volume. Tumor volumes were measured prior to (negative values on the x axis) and after the injections. A "0" on X axis represents the day of the first injection. The tumor volumes were determined from the formula: volume=(length×width×height)/2. Arrows indicate the days when therapy was administered. The error bars represent means±2 standard errors. In FIG. 15(B), representative tumors from virus and PBS treated animals were excised at 42 days post implantation and visually examined. At the onset of viral intratumor injections, tumor sizes appeared similar in size for all three groups of mice (p>0.05). Intratumor treatment with either OncSyn or OncdSyn virus caused a substantial reduction of tumor volumes in comparison to the PBS-treated control group of mice (p<0.05). There was no significant difference in the reduction of tumor sizes in the two viral groups when compared to each other (p>0.05) (FIG. 15A). Analysis of mouse weights during the course of the study did not show significant differences among the three groups, thus the efficacy of treatments was not affected by differential weight gain/loss in the groups (not shown) (p=0.296). Representative tumors were excised immediately after mice were sacrificed. Typically, tumors treated with the PBS control injections appeared substantially larger than those treated with either the OncSyn or OncdSyn viruses (FIG. 15B).

The metastatic potential of the primary 4T1 tumor to internal organs after oncolytic or control therapy was assessed by gross and microscopic pathological examination of internal organs. In the first experimental protocol described above, mouse tumors were allowed to grow to approximately 80-90 mm$^3$, and mice were sacrificed at 42 days post tumor cell implantation. In this experiment, mouse lungs from all three groups of mice (PBS, OncSyn, OncdSyn) had numerous metastatic foci, which were too numerous to be accurately counted (not shown). However, tumor foci in liver and spleen were substantially reduced in OncSyn and OncdSyn-treated mice in comparison to PBS-treated control mice (Table 1). Specifically, all mice in the PBS group had metastatic nodes in liver, spleen, or kidneys. Some of the mice had tumors in all three organs. Importantly, there were no metastatic tumors observed in the kidneys of virus-treated mice (Table 1).

OncdSyn virus reduced tumor volumes equally-well with the OncSyn virus, despite the fact that OncdSyn replicated approximately less than half a log than the OncSyn virus in 4T1 cells. Therefore, the relative increased ability of the OncdSyn virus to destroy tumors in vivo must be attributed to its enhanced fusogenicity.

Metastatic tumor foci in liver and spleen were substantially reduced in OncSyn and OncdSyn-treated mice in comparison to PBS-treated control mice. Reduction of metastatic foci in internal organs (lung, spleen, kidney and liver) was dependent

TABLE 1

Metastatic nodes in internal organs

| Experimental groups | No. of mice in group | No. of mice with metastases in internal organs | No. of mice with metastases in liver | No. of mice with metastases in spleen | No. of mice with metastases in kidney |
|---|---|---|---|---|---|
| PBS | 9 | 9 | 6 | 7 | 3 |
| OncSyn | 7 | 4 | 2 | 2 | 0 |
| OncdSyn | 7 | 3 | 1 | 2 | 0 |

Experimental animals were sacrificed on day 42 post-injection of 4T1 cells and the internal organs were removed and examined for metastases formation by gross pathological evaluation as described above in Example 6.

To better assess the potential of oncolytic virotherapy to reduce metastatic tumors in internal organs, a second experiment was performed in a similar fashion to the previous one with the exception that in the new experiment tumors were allowed to grow to approximately 35-40 mm$^3$ in volume and mice were sacrificed at day 33 post tumor cell implantation after treatment with either OncdSyn or PBS. FIG. 16 illustrates the therapeutic effect of OncdSyn virus on lung metastases. FIGS. 16A and 16B show the gross appearance of excised lungs of representative mice from PBS control and OncdSyn treated groups. FIGS. 16C-16F show lung tissues that were stained with H&E and examined, representative sections for PBS (FIGS. 16C and 16D) and OncdSyn (FIGS. 16E and 16F) groups at 40× (FIGS. 16C, 16E) and 100× (FIGS. 16D, 16F) magnifications.

Lungs of OncdSyn-treated mice appeared to be practically devoid of metastatic tumors with only two mice having two nodes each. In contrast, all PBS-treated mice had multiple metastatic tumors in their lungs (Table 2, FIGS. 16A and 16B). These results were confirmed by pathological examination of paraffin-embedded lung sections stained with Hematoxylin & Eosin (H&E) staining, which revealed the absence of tumors in OncdSyn samples, while PBS-treated control samples had numerous visible tumor foci (FIGS. 16C-16F).

on the size of the original 4T1 tumor, as well as the time of necropsy post implantation of tumor cells. Specifically, there was drastic reduction in tumor foci detected in lungs when the initial tumor size treated with the virus was approximately 35-40 mm$^3$, and necropsies were performed at 33 days after tumor implantation. Furthermore, lungs appeared to have the same number of metastatic foci with PBS-treated controls when the initial treated tumors where 80-90 mm$^3$ and necropsies were performed at day 42 after tumor implantation. This metastatic pattern revealed that lungs were the primary metastatic site of the subcutaneous implanted 4T1 cells. Regardless of the size of the initial tumor treated and the time of necropsies post tumor implantation, the OncSyn and OncdSyn viruses appeared to efficiently reduce the growth of the primary tumor as well as substantially inhibit or eliminate formation of metastatic foci.

It is highly likely that reduction of the primary tumor after oncolytic virotherapy with the OncSyn and OncdSyn viruses is responsible for the observed reduction in the formation of secondary tumor foci, since treatment of the smaller (35-40 mm$^3$) tumors appeared to drastically reduce lung metastases. Alternatively, it is possible that anti-tumor immune responses were elicited by exposure of tumor antigens after destruction of 4T1 cells within the primary tumor by the OncSyn and OncdSyn viruses.

TABLE 2

Metastatic nodes in lungs

| Experimental groups | No. of mice in group | No. of metastatic nodes in lungs of experimental animals[a] | | | | | | | |
|---|---|---|---|---|---|---|---|---|---|
| | | mouse1 | mouse2 | mouse3 | mouse4 | mouse5 | mouse6 | mouse7 | mouse8 |
| PBS | 7 | 3 | 5 | 3 | 18 | 3 | 10 | 1 | |
| OncdSyn | 8 | 2 | 0 | 0 | 0 | 2 | 0 | 0 | 0 |

Experimental animals in PBS and OncdSyn groups were sacrificed on day 33 post-inoculation of 4T1 cells and the lungs were removed and examined for metastatic node formation as described above in Example 6.
[a]PBS > OncdSyn (Wilcoxon Two-Sample test, p = 0.002).

Both OncSyn and OncdSyn viruses substantially reduced the growth of 4T1 tumors compared to the PBS controls, despite the fact that these viruses did not efficiently replicate in 4T1 cells in cell culture. Apparently, viral replication and infectious virus production in cell cultures did not correlate with the oncolytic efficacy of these viruses, because the The OncdSyn virus caused extensive virus-induced cell fusion and fused Hep-2 cells, while the OncSyn virus did not (Data not shown). Furthermore, the OncdSyn virus caused more extensive fusion than OncSyn in both Vero and 4T1 cells. The OncdSyn virus appeared to produce intact syncytia that remained attached to the cell culture flasks, while the OncSyn virus-induced syncytia contained infected single cells, which detached easier than the OncdSyn-infected syncytia. This phenomenon has been previously observed for the gB and gK syncytial mutations and it is probably due, in part, to the extensive virus-induced cell fusion caused by the gK syncytial mutation, which appears to also fuse internal membranes such as nuclear membranes in addition to plasma membranes of cells (Data not shown). Viral titers of the OncdSyn virus were lower in Vero cells than titers of the OncSyn virus and substantially lower than titers of the OncSyn virus in 4T1 cells. The increased ability of the OncdSyn virus to cause extensive virus-induced cell fusion is probably responsible for the observed decrease in viral titers in comparison to the OncSyn virus.

Overall, these results show that both OncSyn and OncdSyn viruses can efficiently reduce the primary and metastatic growth of 4T1 tumors established in immunocompetent mice. It is expected that these viruses would be even more efficacious against human breast cancer tumors by virtue of the fact that they can replicate substantially more efficiently (more than one log) in human than mouse cells. The availability of both OncSyn and OncdSyn viruses as bacterial artificial chromosomes will enable the generation of additional recombinant viruses that carry multiple anti-tumor and immunomodulatory transgenes, which could further enhance the anti-tumor efficacy of these viruses.

REFERENCES

ADVANI, S. J., CHUNG, S. M., YAN, S. Y., GILLESPIE, G. Y., MARKERT, J. M., WHITLEY, R. J., ROIZMAN, B., and WEICHSELBAUM, R. R. (1999). Replication-competent, nonneuroinvasive genetically engineered herpes virus is highly effective in the treatment of therapy-resistant experimental human tumors. Cancer Res 59, 2055-2058.

ANDREANSKY, S., SOROCEANU, L., FLOTTE, E. R., CHOU, J., MARKERT, J. M., GILLESPIE, G. Y., ROIZMAN, B., and WHITLEY, R. J. (1997). Evaluation of genetically engineered herpes simplex viruses as oncolytic agents for human malignant brain tumors. Cancer Res 57, 1502-1509.

ARGNANI, R., LUFINO, M., MANSERVIGI, M., and MANSERVIGI, R. (2005). Replication-competent herpes simplex vectors: design and applications. Gene Ther 12 Suppl 1, S170-177.

ASLAKSON, C. J., and MILLER, F. R. (1992). Selective events in the metastatic process defined by analysis of the sequential dissemination of subpopulations of a mouse mammary tumor. Cancer Res 52, 1399-1405.

BAGHIAN, A., CHOULJENKO, V. N., DAUVERGNE, O., NEWMANT, M. J., BAGHIAN, S., and KOUSOULAS, K. G. (2002). Protective immunity against lethal HSV-1 challenge in mice by nucleic acid-based immunisation with herpes simplex virus type-1 genes specifying glycoproteins gB and gD. J Med Microbiol 51, 350-357.

BAGHIAN, A., DIETRICH, M. A., and KOUSOULAS, K. G. (1992). Cell fusion caused by herpes simplex virus-1 (HSV-1) strains tsB5 and MP is inhibited at pH 6.7 and pH 7.0. Arch Virol 122, 119-131.

BAO, L., MATSUMURA, Y., BABAN, D., SUN, Y., and TARIN, D. (1994). Effects of inoculation site and Matrigel on growth and metastasis of human breast cancer cells. Br J Cancer 70, 228-232.

BENNETT, J. J., DELMAN, K. A., BURT, B. M., MARIOTTI, A., MALHOTRA, S., ZAGER, J., PETROWSKY, H., MASTORIDES, S., FEDEROFF, H., and FONG, Y. (2002). Comparison of safety, delivery, and efficacy of two oncolytic herpes viruses (G207 and NV1020) for peritoneal cancer. Cancer gene therapy 9, 935-945.

BZIK, D. J., FOX, B. A., DELUCA, N. A., and PERSON, S. (1984a). Nucleotide sequence of a region of the herpes simplex virus type 1 gB glycoprotein gene: mutations affecting rate of virus entry and cell fusion. Virology 137, 185-190.

BZIK, D. J., FOX, B. A., DELUCA, N. A., and PERSON, S. (1984b). Nucleotide sequence specifying the glycoprotein gene, gB, of herpes simplex virus type 1. Virology 133, 301-314.

CAILLOU, R., OLIVE, M, CRUCIGER, QVJ. (1978). Long-term human breast carcinoma cell lines of metastatic origin: preliminary characterization. In vitro 14, 911-915.

CAREW, J. F., KOOBY, D. A., HALTERMAN, M. W., KIM, S. H., FEDEROFF, H. J., and FONG, Y. (2001). A novel approach to cancer therapy using an oncolytic herpes virus to package amplicons containing cytokine genes. Mol Ther 4, 250-256.

CAVALCOLI, J. D., BAGHIAN, A., HOMA, F. L., and KOUSOULAS, K. G. (1993). Resolution of genotypic and phenotypic properties of herpes simplex virus type 1 temperature-sensitive mutant (KOS) tsZ47: evidence for allelic complementation in the UL28 gene. Virology 197, 23-34.

COZZI, P. J., BURKE, P. B., BHARGAV, A., HESTON, W. D., HURYK, B., SCARDINO, P. T., and FONG, Y. (2002). Oncolytic viral gene therapy for prostate cancer using two attenuated, replication-competent, genetically engineered herpes simplex viruses. Prostate 53, 95-100.

COZZI, P. J., MALHOTRA, S., MCAULIFFE, P., KOOBY, D. A., FEDEROFF, H. J., HURYK, B., JOHNSON, P., SCARDINO, P. T., HESTON, W. D., and FONG, Y. (2001). Intravesical oncolytic viral therapy using attenuated, replication-competent herpes simplex viruses G207 and Nv1020 is effective in the treatment of bladder cancer in an orthotopic syngeneic model. Faseb J 15, 1306-1308.

CROSS, D., and BURMESTER J. K. (2006). Gene therapy for cancer treatment: Past, present and future. Clinical Medicine & Research 4, 218-227.

DEBROY, C., PEDERSON, N., and PERSON, S. (1985). Nucleotide sequence of a herpes simplex virus type 1 gene that causes cell fusion. Virology 145, 36-48.

DIAZ, R. M., BATEMAN, A., EMILIUSEN, L., FIELDING, A., TRONO, D., RUSSELL, S. J., and VILE, R. G. (2000). A lentiviral vector expressing a fusogenic glycoprotein for cancer gene therapy. Gene Ther 7, 1656-1663.

EBRIGHT, M. I., ZAGER, J. S., MALHOTRA, S., DELMAN, K. A., WEIGEL, T. L., RUSCH, V. W., and FONG, Y. (2002). Replication-competent herpes virus NV1020 as direct treatment of pleural cancer in a rat model. J Thorac Cardiovasc Surg 124, 123-129.

FOSTER, T. P., ALVAREZ, X., and KOUSOULAS, K. G. (2003). Plasma membrane topology of syncytial domains of herpes simplex virus type 1 glycoprotein K (gK): the UL20 protein enables cell surface localization of gK but not gK-mediated cell-to-cell fusion. J Virol 77, 499-510.

FOSTER, T. P., CHOULJENKO, V. N., and KOUSOULAS, K. G. (1999). Functional characterization of the HveA homolog specified by African green monkey kidney cells with a herpes simplex virus expressing the green fluorescence protein. Virology 258, 365-374.

FOSTER, T. P., and KOUSOULAS, K. G. (1999). Genetic analysis of the role of herpes simplex virus type 1 glycoprotein K in infectious virus production and egress. J Virol 73, 8457-8468.

FOSTER, T. P., MELANCON, J. M., BAINES, J. D., and KOUSOULAS, K. G. (2004a). The herpes simplex virus type 1 UL20 protein modulates membrane fusion events during cytoplasmic virion morphogenesis and virus-induced cell fusion. J Virol 78, 5347-5357.

FOSTER, T. P., MELANCON, J. M., and KOUSOULAS, K. G. (2001a). An alpha-helical domain within the carboxyl terminus of herpes simplex virus type 1 (HSV-1) glycoprotein B (gB) is associated with cell fusion and resistance to heparin inhibition of cell fusion. Virology 287, 18-29.

FOSTER, T. P., MELANCON, J. M., OLIVIER, T. L., and KOUSOULAS, K. G. (2004b). Herpes simplex virus type 1 glycoprotein K and the UL20 protein are interdependent for intracellular trafficking and trans-Golgi network localization. J Virol 78, 13262-13277.

FOSTER, T. P., RYBACHUK, G. V., and KOUSOULAS, K. G. (1998). Expression of the enhanced green fluorescent protein by herpes simplex virus type 1 (HSV-1) as an in vitro or in vivo marker for virus entry and replication. J Virol Methods 75, 151-160.

FOSTER, T. P., RYBACHUK, G. V., and KOUSOULAS, K. G. (2001b). Glycoprotein K specified by herpes simplex virus type 1 is expressed on virions as a Golgi complex-dependent glycosylated species and functions in virion entry. J Virol 75, 12431-12438.

FOSTER, T. P., et al., "Functional and physical interactions of the herpes simplex virus type 1 UL20 membrane protein with glycoprotein K," In press in the Journal of Virology (expected July 2008).

FU, X., TAO, L., JIN, A., VILE, R., BRENNER, M. K., and ZHANG, X. (2003). Expression of a fusogenic membrane glycoprotein by an oncolytic herpes simplex virus potentiates the viral antitumor effect. Mol Ther 7, 748-754.

FU, X., and ZHANG, X. (2002). Potent systemic antitumor activity from an oncolytic herpes simplex virus of syncytial phenotype. Cancer Res 62, 2306-2312.

HACKETT, A. J., SMITH, H. S., SPRINGER, E. L., OWENS, R. B., NELSON-REES, W. A., RIGGS, J. L., and GARDNER, M. B. (1977). Two syngeneic cell lines from human breast tissue: the aneuploid mammary epithelial (Hs578T) and the diploid myoepithelial (Hs578Bst) cell lines. J Natl Cancer Inst 58, 1795-1806.

HOFFMANN, D., BAYER, W., AND WILDNER, O. (2007). Local and distant immune-mediated control of colon cancer growth with fusogenic membrane glycoproteins in combination with viral oncolysis. Hum Gene Ther 18(5), 435-50.

HU, J. C., and COFFIN, R. S. (2003). Oncolytic herpes simplex virus for tumor therapy. Int Rev Neurobiol 55, 165-184.

JEYARETNA, D. S., AND KURODA, T. (2007). Recent advances in the development of oncolytic HSV-1 vectors: 'arming' of HSV-1 vectors and application of bacterial artificial chromosome technology for their construction. Curr Opin Mol Ther 9(5), 447-66.

KEMENY, N., BROWN, K., COVEY, A., KIM, T., BHARGAVA, A., BRODY, L., GUILFOYLE, B., HAAG, N. P., KARRASCH, M., GLASSCHROEDER, B., KNOLL, A., GETRAJDMAN, G., KOWAL, K. J., JARNAGIN, W. R., and FONG, Y. (2006). Phase I, Open-Label, Dose-Escalating Study of a Genetically Engineered Herpes Simplex Virus, NV1020, in Subjects with Metastatic Colorectal Carcinoma to the Liver. Hum Gene Ther 17, 1214-1224.

KOSHIZUKA, K., KOIKE, M., ASOU, H., CHO, S. K., STEPHEN, T., RUDE, R. K., BINDERUP, L., USKOKOVIC, M., and KOEFFLER, H. P. (1999). Combined effect of vitamin D3 analogs and paclitaxel on the growth of MCF-7 breast cancer cells in vivo. Breast Cancer Res Treat 53, 113-120.

KRAMM, C. M., CHASE, M., HERRLINGER, U., JACOBS, A., PECHAN, P. A., RAINOV, N. G., SENA-ESTEVES, M., AGHI, M., BARNETT, F. H., CHIOCCA, E. A., and BREAKEFIELD, X. O. (1997). Therapeutic efficiency and safety of a second-generation replication-conditional HSV1 vector for brain tumor gene therapy. Hum Gene Ther 8, 2057-2068.

LEUSCHNER, C., ENRIGHT, F. M., GAWRONSKA, B., and HANSEL, W. (2003). Membrane disrupting lytic peptide conjugates destroy hormone dependent and independent breast cancer cells in vitro and in vivo. Breast Cancer Res Treat 78, 17-27.

LI, H., DUTUOR, A., FU, X., AND ZHANG, X. (2007). Induction of strong antitumor immunity by an HSV-2-based oncolytic virus in a murine mammary tumor model. J Gene Med 9(3), 161-9.

LIU, B. L., ROBINSON, M., HAN, Z. Q., BRANSTON, R. H., ENGLISH, C., REAY, P., MCGRATH, Y., THOMAS, S. K., THORNTON, M., BULLOCK, P., LOVE, C. A., and COFFIN, R. S. (2003). ICP34.5 deleted herpes simplex virus with enhanced oncolytic, immune stimulating, and anti-tumour properties. Gene Ther 10, 292-303.

MANSERVIGI, R., SPEAR, P. G., AND BUCHAN, A. (1977). Cell fusion induced by herpes simplex virus is promoted and suppressed by different viral glycoproteins. Proc Natl Acad Sci USA 74(9), 3913-7.

MEIGNIER, B., LONGNECKER, R., and ROIZMAN, B. (1988). In vivo behavior of genetically engineered herpes simplex viruses R7017 and R7020: construction and evaluation in rodents. J Infect Dis 158, 602-614.

MEIGNIER, B., MARTIN, B., WHITLEY, R. J., and ROIZMAN, B. (1990). In vivo behavior of genetically engineered herpes simplex viruses R7017 and R7020. II. Studies in immunocompetent and immunosuppressed owl monkeys (*Aotus trivirgatus*). J Infect D is 162, 313-321.

MELANCON, J. M., FOSTER, T. P., and KOUSOULAS, K. G. (2004). Genetic analysis of the herpes simplex virus type 1 UL20 protein domains involved in cytoplasmic virion envelopment and virus-induced cell fusion. J Virol 78, 7329-7343.

MELANCON, J. M., LUNA, R. E., FOSTER, T. P., and KOUSOULAS, K. G. (2005). Herpes simplex virus type 1 gK is required for gB-mediated virus-induced cell fusion, while neither gB and gK nor gB and UL20p function redundantly in virion de-envelopment. J Virol 79, 299-313.

MELANCON, J. M., FULMER, P. A., and KOUSOULAS, K. G. (2007). The herpes simplex virus UL20 protein functions in glycoprotein K (gK) intracellular transport and virus-induced cell fusion are independent of UL20 functions in cytoplasmic virion envelopment. J Virol 4, 120.

MILLER, C. G., AND FRASER, N. W. (2000). Role of the immune response during neuro-attenuated herpes simplex virus-mediated tumor destruction in a murine intracranial melanoma model. Cancer Res 60(20), 5714-22.

MILLER, C. G., AND FRASER, N. W. (2003). Requirement of an integrated immune response for successful neuroattenuated HSV-1 therapy in an intracranial metastatic melanoma model. Mol Ther 7(6), 741-7.

MULLEN, J. T., DONAHUE, J. M., CHANDRASEKHAR, S., YOON, S. S., LIU, W., ELLIS, L. M., NAKAMURA, H., KASUYA, H., PAWLIK, T. M., and TANABE, K. K. (2004). Oncolysis by viral replication and inhibition of angiogenesis by a replication-conditional herpes simplex virus that expresses mouse endostatin. Cancer 101, 869-877.

NAKAMORI, M., FU, X., ROUSSEAU, R., CHEN, S. Y., and ZHANG, X. (2004). Destruction of nonimmunogenic mammary tumor cells by a fusogenic oncolytic herpes simplex virus induces potent antitumor immunity. Mol Ther 9, 658-665.

NAKAMURA, H., MULLEN, J. T., CHANDRASEKHAR, S., PAWLIK, T. M., YOON, S. S., and TANABE, K. K. (2001). Multimodality therapy with a replication-conditional herpes simplex virus 1 mutant that expresses yeast cytosine deaminase for intratumoral conversion of 5-fluorocytosine to 5-fluorouracil. Cancer Res 61, 5447-5452.

PELLETT, P. E., KOUSOULAS, K. G., PEREIRA, L., and ROIZMAN, B. (1985). Anatomy of the herpes simplex virus 1 strain F glycoprotein B gene: primary sequence and predicted protein structure of the wild type and of monoclonal antibody-resistant mutants. J Virol 53, 243-253.

PELLINEN, R., HAKKARAINEN, T., WAHLFORS, T., TULIMAKI, K., KETOLA, A., TENHUNEN, A., SALONEN, T., and WAHLFORS, J. (2004). Cancer cells as targets for lentivirus-mediated gene transfer and gene therapy. Int J Oncol 25, 1753-1762.

PULASKI, B. A., AND OSTRAND-ROSENBERG, S. (1998). Reduction of established spontaneous mammary carcinoma metastases following immunotherapy with major histocompatibility complex class 11 and B7.1 cell-based tumor vaccines. Cancer Res 58(7), 1486-93.

SHEN, Y., and NEMUNAITIS, J. (2006). Herpes simplex virus 1 (HSV-1) for cancer treatment. Cancer gene therapy 13, 975-992.

TANAKA, M., KAGAWA, H., YAMANASHI, Y., SATA, T., and KAWAGUCHI, Y. (2003). Construction of an excisable bacterial artificial chromosome containing a full-length infectious clone of herpes simplex virus type 1: viruses reconstituted from the clone exhibit wild-type properties in vitro and in vivo. J Virol 77, 1382-1391.

TISCHER, B. K., VON EINEM, J., KAUFER, B., AND OSTERRIEDER, N. (2006). Two-step red-mediated recombination for versatile high-efficiency markerless DNA manipulation in *Escherichia coli*. Biotechniques 40(2), 191-7.

TODO, T., RABKIN, S. D., SUNDARESAN, P., WU, A., MEEHAN, K. R., HERSCOWITZ, H. B., AND MARTUZA, R. L. (1999). Systemic antitumor immunity in experimental brain tumor therapy using a multimutated, replication-competent herpes simplex virus. Hum Gene Ther 10(17), 2741-55.

TODO, T. (2002). Oncolytic virus therapy using genetically engineered herpes simplex viruses. Hum Cell 15, 151-159.

TODO, T., MARTUZA, R. L., RABKIN, S. D., and JOHNSON, P. A. (2001). Oncolytic herpes simplex virus vector with enhanced MHC class I presentation and tumor cell killing. Proc Natl Acad Sci USA 98, 6396-6401.

WILSON, M. J., and SINHA, A. A. (1997). Human prostate tumor angiogenesis in nude mice: metalloprotease and plasminogen activator activities during tumor growth and neovascularization of subcutaneously injected matrigel impregnated with human prostate tumor cells. Anat Rec 249, 63-73.

VAHA-KOSKELA, M. J. V., HEIKKILA, J. E., and HINKANEN, A. E. (2007). Oncolytic viruses in cancer therapy. Cancer Letters 254, 178-216.

The complete disclosures of all references cited in this specification are hereby incorporated by reference. Also incorporated by reference are the complete disclosures of the following: A. H. Israyelyan et al., "Effective treatment of human breast tumor in a mouse xenograpt model with Herpes Simplex Virus Type 1 specifying the NV1020 genomic deletion and the gBsyn3 syncytial mutation enabling high viral replication and spread in breast cancer cells," Human Gene Therapy, vol. 18, pp. 457-73 (2007), published online on May 14, 2007; A. Israyelyan et al., "NV1020-like herpes simplex virus type-1 oncolytic and highly fusogenic mutants effectively inhibit primary and metastatic tumors in mice." In press in the Virology Journal (expected May 2008); Foster, T. P., et al., "Functional and physical interactions of the herpes simplex virus type 1 UL20 membrane protein with glycoprotein K." In press in the Journal of Virology (expected July 2008); and A. T. David et al., "The herpes simplex virus type-1 (HSV-1) glycoprotein K (gK) is essential for viral corneal spread and neuroinvasiveness," in press in Current Eye Research (expected May 2008). In the event of an otherwise irreconcilable conflict, however, the present specification shall control.

What is claimed:

1. A recombinant, replication-competent herpes simplex virus whose genome concurrently lacks the coding sequence for a single $\gamma_1$ 34.5 gene and comprises a mutated UL27(gB) gene, wherein the mutated UL27(gB) gene encodes gBsyn3, and wherein the expression of gBsyn3 substantially increases the ability of the virus to promote virus-induced cell fusion.

2. The virus as in claim 1, wherein the virus is herpes simplex virus type 1.

3. The virus as in claim 1, wherein the virus is herpes simplex virus type 2.

4. The virus as in claim 1, wherein the genome additionally comprises a mutated UL53 (gK) gene, wherein the mutated UL53 (gK) gene encodes gKsyn1, wherein the expression of gKsyn1 substantially increases the ability of the virus to promote virus-induced cell fusion.

5. A vaccine for herpes simplex viral infections comprising The virus as in claim 4.

6. The virus as in claim 1, wherein the herpes simplex virus genome further comprises a nucleotide sequence encoding one or more desired proteins operably linked to a regulatory promoter.

7. The virus as in claim 6, wherein the one or more desired proteins are selected from the group consisting of immunomodulatory proteins, cytolytic peptides, siRNAs, prodrug converting enzymes, and angiogenesis inhibitors.

8. The virus as in claim 6, wherein the regulatory promoter is selected from the group consisting of a viral promoter, a tumor-specific promoter, and a mammalian promoter.

9. The virus as in claim 1, wherein the viral genome additionally lacks the coding sequence of one or more single genes selected from the group comprising UL56, $\alpha 0$, $\alpha 4$, and LAT.

10. The virus as in claim 1, wherein the viral genome additionally comprises deletions in the UL56, $\alpha 0$, $\alpha 4$, and LAT genes.

11. A composition comprising the herpes simplex virus of claim 1 and a pharmaceutically acceptable vehicle for said virus.

12. A method for treating a tumor in a mammal, comprising administering to the mammal with the tumor a therapeutic amount of the herpes simplex virus as in claim 1.

13. The method of claim 12, wherein the tumor is selected from the group consisting of brain tumor, pancreatic tumor, breast tumor, colorectal tumor, peritoneal tumor, prostate tumor, and other solid tumors.

14. The method of claim 12, wherein the tumor is a breast tumor.

15. The method of claim 12, wherein the virus is administered by intratumor injection.

16. The method of claim 12, wherein the virus is administered by intravascular injection proximally to the tumor.

17. A bacterial artificial chromosome that comprises a herpes simplex virus genome that lacks the coding sequence for a single $\gamma_1$ 34.5 gene and that comprises a mutated UL27(gB) gene, wherein the mutated UL27(gB) gene encodes gBsyn3, and wherein the expression of gBsyn3 substantially increases the ability of a virus to promote virus-induced cell fusion.

* * * * *